(12) United States Patent
Kelly et al.

(10) Patent No.: US 12,168,643 B2
(45) Date of Patent: *Dec. 17, 2024

(54) COMPOUNDS FOR THE TREATMENT OF NEUROMUSCULAR DISORDERS

(71) Applicant: NMD PHARMA A/S, Aarhus N (DK)

(72) Inventors: Nicholas Kelly, Bagsværd (DK); Lars J.S. Knutsen, Essex (GB); Daniel Paul Cotton, Nottingham (GB)

(73) Assignee: NMD PHARMA A/S, Aarhus N (DK)

( * ) Notice: Subject to any disclaimer, the term of this patent is extended or adjusted under 35 U.S.C. 154(b) by 259 days.

This patent is subject to a terminal disclaimer.

(21) Appl. No.: 17/619,329

(22) PCT Filed: Jun. 19, 2020

(86) PCT No.: PCT/EP2020/067064
§ 371 (c)(1),
(2) Date: Dec. 15, 2021

(87) PCT Pub. No.: WO2020/254553
PCT Pub. Date: Dec. 24, 2020

(65) Prior Publication Data
US 2022/0306564 A1     Sep. 29, 2022

(30) Foreign Application Priority Data
Jun. 19, 2019 (EP) .................... 19181240

(51) Int. Cl.
*C07C 59/72* (2006.01)
*A61P 21/00* (2006.01)

(52) U.S. Cl.
CPC .............. *C07C 59/72* (2013.01); *A61P 21/00* (2018.01); *C07C 2601/16* (2017.05)

(58) Field of Classification Search
CPC ................................ C07C 59/72; A61P 21/00
See application file for complete search history.

(56) References Cited

U.S. PATENT DOCUMENTS 10,385,028 B2 * 8/2019 Knutsen ............... C07D 213/30

FOREIGN PATENT DOCUMENTS

WO     2016202341 A1    12/2016

OTHER PUBLICATIONS

International Search Report (PCT/ISA/210) and Written Opinion (PCT/ISA/237) mailed on Aug. 25, 2020, by the European Patent Office as the International Searching Authority for International Application No. PCT/EP2020/067064. (9 pages).

* cited by examiner

*Primary Examiner* — Sikarl A Witherspoon
(74) *Attorney, Agent, or Firm* — BUCHANAN, INGERSOLL & ROONEY PC

(57) ABSTRACT

The present disclosure relates to compounds of Formula I:

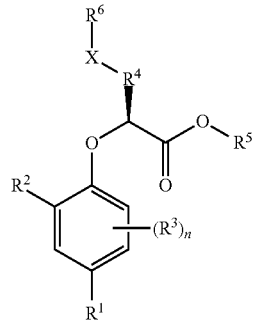

Formula I suitable for treating, ameliorating and/or preventing neuromuscular disorders, including the reversal of drug-induced neuromuscular blockade. The compounds as defined herein preferably inhibit the ClC-1 ion channel.

20 Claims, 2 Drawing Sheets

COMPOUNDS FOR THE TREATMENT OF NEUROMUSCULAR DISORDERS

TECHNICAL FIELD

The present disclosure relates to compounds and their use in treating, ameliorating and/or preventing neuromuscular disorders, including the reversal of drug-induced neuromuscular blockade. The compounds as defined herein preferably inhibit the ClC-1 ion channel. The disclosure further relates to methods of treating, preventing and/or ameliorating neuromuscular disorders, by administering said composition to a person in need thereof.

BACKGROUND

Walking, breathing, and eye movement are examples of essential everyday physiological activities that are powered by the contractile activity of skeletal muscle. Skeletal muscles are inherently in a resting state and contractile activity occurs exclusively in response to commands from the central nervous system (CNS). Such neuronal commands take the form of action potentials that travel from the brain to the muscle fibres in several steps. The neuromuscular junction (NMJ) is a highly specialized membrane area on muscle fibres where motor neurons come into close contact with the muscle fibres, and it is at the NMJ where neuronal action potentials are transmitted to muscular action potentials in a one-to-one fashion via synaptic transmission.

Neuromuscular transmission refers to the sequence of cellular events at the NMJ whereby an action potential in the lower motor neuron is transmitted to a corresponding action potential in a muscle fibre (Wood S J, Slater C R. Safety factor at the neuromuscular junction. *Prog. Neurobiol.* 2001, 64, 393-429). When a neuronal action potential arrives at the pre-synaptic terminal it triggers influx of $Ca^{2+}$ through voltage gated P/Q-type $Ca^{2+}$ channels in the nerve terminal membrane. This influx causes a rise in cytosolic $Ca^{2+}$ in the nerve terminal that triggers exocytosis of acetylcholine (ACh). Released ACh next diffuses across the synaptic cleft to activate nicotinic ACh receptors in the post-synaptic, muscle fibre membrane. Upon activation, ACh receptors convey an excitatory current flow of $Na^+$ into the muscle fibre, which results in a local depolarization of the muscle fibre at the NMJ that is known as the endplate potential (EPP). If the EPP is sufficiently large, voltage gated $Na^+$ channels in the muscle fibre will activate and an action potential in the muscle fibre will ensue. This action potential then propagates from the NMJ throughout the muscle fibre and triggers release of $Ca^{2+}$ release from the sarcoplasmic reticulum. The released $Ca^{2+}$ activates the contractile proteins within the muscle fibres, thus resulting in contraction of the fibre.

Failure of neuromuscular transmission can arise from both pre-synaptic dysfunction [Lambert Eaton syndrome (Titulaer M J, Lang B, Verschuuren J J. Lambert-Eaton myasthenic syndrome: from clinical characteristics to therapeutic strategies. *Lancet Neurol.* 2011, 10, 1098-107), amyotrophic lateral sclerosis (Killian J M, Wilfong A A, Burnett L, Appel S H, Boland D. Decremental motor responses to repetitive nerve stimulation in ALS. *Muscle Nerve,* 1994, 17, 747-754), spinal muscular atrophy (Wadman R I, Vrancken A F, van den Berg L H, van der Pol W L. Dysfunction of the neuromuscular junction in spinal muscular atrophy types 2 and 3. *Neurology,* 2012, 79, 2050-2055) and as a result of post-synaptic dysfunction as occurs in myasthenia gravis (Le Panse R, Berrih-Aknin S. Autoimmune myasthenia gravis: autoantibody mechanisms and new developments on immune regulation. *Curr Opin Neurol.,* 2013, 26, 569-576)]. Failure to excite and/or propagate action potentials in muscle can also arise from reduced muscle excitability such as in critical illness myopathy (CIM) (Latronico, N., Bolton, C. F. Critical illness polyneuropathy and myopathy: a major cause of muscle weakness and paralysis. *Lancet Neurol.* 2011, 10, 931-941). In Lambert Eaton syndrome, an autoimmune attack against the pre-synaptic P/Q-type $Ca^{2+}$ channels results in markedly reduced $Ca^{2+}$ influx into the nerve terminal during the pre-synaptic action potential and consequently a reduced release of ACh into the synaptic cleft. In myasthenia gravis, the most common finding is an autoimmune attack on the post-synaptic membrane either against the nicotinic ACh receptors or the musk-receptor in the muscle fibre membrane. Congenital forms of myasthenia are also known. Common to disorders with neuromuscular transmission failure (Lambert Eaton syndrome, amyotrophic lateral sclerosis, spinal muscular atrophy and myasthenia gravis) is that the current flow generated by ACh receptor activation is markedly reduced, and EPPs therefore become insufficient to trigger muscle fibre action potentials.

Neuromuscular blocking agents also reduce EPP by antagonizing ACh receptors. In CIM with reduced muscle excitability, the EPP may be of normal amplitude but they are still insufficient to trigger muscle fibre action potentials because the membrane potential threshold for action potential excitation has become more depolarized because of loss of function of voltage gated $Na^+$ channels in the muscle fibres.

While ACh release (Lambert Eaton, amyotrophic lateral sclerosis, spinal muscular atrophy), ACh receptor function (myasthenia gravis, neuromuscular blockade) and function of voltage gated $Na^+$ channels (CIM) are essential components in the synaptic transmission at NMJ, the magnitude of the EPP is also affected by inhibitory currents flowing in the NMJ region of muscle fibres. These currents tend to outbalance excitatory current through ACh receptors and, expectedly, they thereby tend to reduce EPP amplitude. The most important ion channel for carrying such inhibitory membrane currents in muscle fibres is the muscle-specific ClC-1 $Cl^-$ ion channel (Kwieciński H, Lehmann-Horn F, Rüdel R. Membrane currents in human intercostal muscle at varied extracellular potassium. *Muscle Nerve.* 1984, 7, 465-469; Kwieciński H, Lehmann-Horn F, Rüdel R. Drug-induced myotonia in human intercostal muscle. *Muscle Nerve.* 1988, 11, 576-581; Pedersen, T. H., F. de Paoli, and O. B. Nielsen. Increased excitability of acidified skeletal muscle: role of chloride conductance. *J. Gen. Physiol.,* 2005, 125, 237-246).

ACh esterase (AChE) inhibitors are traditionally used in the treatment of myasthenia gravis. This treatment leads to improvement in most patients but it is associated with side effects, some of which are serious (Mehndiratta M M, Pandey S, Kuntzer T. Acetylcholinesterase inhibitor treatment for myasthenia gravis. *Cochrane Database Syst Rev.* 2014, Oct. 13; 10). Because ACh is an import neurotransmitter in the autonomic nervous system, delaying its breakdown can lead to gastric discomfort, diarrhoea, salivation and muscle cramping. Overdosing is a serious concern as it can lead to muscle paralysis and respiratory failure, a situation commonly referred to as cholinergic crisis. Despite the serious side effects of AChE inhibitors, these drugs are today the treatment of choice for a number of disorders involving neuromuscular impairment. In patients where pyridostigmine (a parasympathomimetic and a reversible AChE inhibitor) is insufficient, corticosteroid treatment (prednisone) and immunosuppressive treatment (azathioprine) is used. Plasma exchange can be used to obtain a fast but transient improvement.

Unfortunately, all of the currently employed drug regimens for treatment of myasthenia gravis are associated with deleterious long-term consequences (Howard, J. F. Jr. Adverse drug effects on neuromuscular transmission. *Semin Neurol.* 1990, 10, 89-102) despite research to identify new treatments (Gilhus, N. E. New England Journal of Medicine, 2016, 375, 2570-2581).

The ClC-1 ion channel (Pedersen, T. H., Riisager, A., Vincenzo de Paoli, F., Chen, T-Y, Nielsen, O. B. Role of physiological ClC-1 Cl⁻ ion channel regulation for the excitability and function of working skeletal muscle. *J. Gen. Physiol.* 2016, 147, 291-308) is emerging as a target for potential drugs, although its potential has been largely unrealised.

There have been publications of various ligands at the ClC-1 ion channels, see for example: Liantonio, A., Accardi, A., Carbonara, G., Fracchiolla, G., Loiodice, F., Tortorella P, Traverso S, Guida P, Pierno S, De Luca A, Camerino D C, Pusch M. Molecular requisites for drug binding to muscle ClC-1 and renal ClC-K channel revealed by the use of phenoxy-alkyl derivatives of 2-(p-chlorophenoxy)propionic acid. *Mol. Pharmacol.*, 2002, 62, 265-271 and Liantonio, A. et al., Structural requisites of 2-(p-chlorophenoxy)propionic acid analogues for activity on native rat skeletal muscle chloride conductance and on heterologously expressed CLC-1. *Br. J. Phamacol.*, 2003, 129, 1255-1264.

In the article Liantonio, A., Pusch, M., Picollo, A., Guida, P., De Luca, A., Pierno, S., Fracchiolla, G., Loiodice, F., Tortorella, P., Conte-Camerino, D. Investigations of pharmacologic properties of the renal ClC-K1 chloride channel co-expressed with barttin by the use of 2-(p-chlorophenoxy) propionic acid derivatives and other structurally unrelated chloride channels blockers. *Journal of the American Society of Nephrology,* 2004, 15, 13-20, ligands for ClC-K1 chloride channels were disclosed.

In the publication Pusch, M., Liantonio, A., Bertorello, L., Accardi, A., De Luca, A., Pierno, S., Tortorella, V., Conte-Camerino, D. Pharmacological characterization of chloride channels belonging to the ClC family by the use of chiral clofibric acid derivatives. *Molecular Pharmacology,* 2000, 58, 498-507, the authors disclosed effects of enantiomers of 2-(p-chlorophenoxy)propionic acid on ClC-1 and ClC-2 ion channels.

In the article Ferorelli, S., Loiodice, F., Tortorella, V., Conte-Camerino, D., De Luca, A. M. Carboxylic acids and skeletal muscle chloride channel conductance: effects on the biological activity induced by the introduction of methyl groups on the aromatic ring of chiral α-(4-chloro-phenoxy) alkanoic acids, *Farmaco,* 2001, 56, 239-246, derivatives of (4-chloro-phenoxy)alkanoic acids were tested for skeletal muscle chloride conductance.

Edoardo Aromataris investigated 4-chlorophenoxyisobutyric acid derivatives in his PhD thesis "Pharmacology of the ClC-1 Chloride Channel"; see: https://digital.library.adelaide.edu.au/dspace/bitstream/2440/58973/8/02whole.pdf In WO 2016/202341, Pedersen et al. reported a series of phenoxypropionic acids and related compounds that appear to block the ClC-1 ion channel for use in treating, ameliorating and/or preventing neuromuscular disorders. However, they possess alternative structural features to those in the current disclosure.

SUMMARY

The present disclosure comprises a new series of compounds that alleviate disorders of the neuromuscular junction through inhibition of ClC-1 channels.

It has been found that a set of novel compounds that inhibit ClC-1 ion channels are capable of restoring neuromuscular transmission, as evidenced by the data generated by investigation of the compound set in biological models described herein. These compounds thus constitute a new group of potential drugs that can be used to treat or ameliorate muscle weakness and muscle fatigue in neuromuscular junction disorders caused by disease or by neuromuscular blocking agents.

The present disclosure thus concerns the discovery of new ClC-1 ion channel inhibitors with application in the treatment of a range of conditions, such as reversal of block, ALS and myasthenic conditions, in which muscle activation by the nervous system is compromised and symptoms of weakness and fatigue are prominent.

In one aspect, the disclosure concerns a compound of Formula (I):

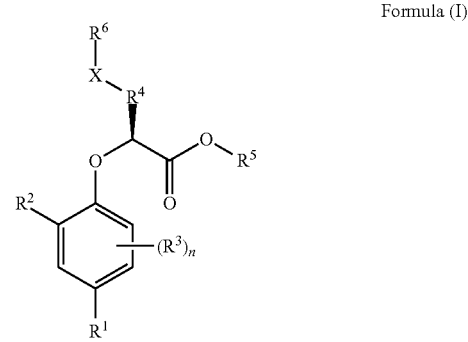

Formula (I)

wherein:
R¹ is selected from the group consisting of F, Cl, Br and I;
R² is selected from the group consisting of $C_{2-5}$ alkyl optionally substituted with one or more, identical or different, substituents R⁸ and $C_{3-5}$ cycloalkyl optionally substituted with one or more, identical or different, substituents R⁸ and wherein one —CH₂— in the $C_{2-5}$ alkyl or $C_{3-5}$ cycloalkyl is optionally replaced by —O—;
R³ is selected from the group consisting of deuterium, Cl and F;
R⁴ is $C_{1-3}$ alkanediyl which may be optionally substituted with one or more, identical or different, substituents R⁸;
R⁵ is selected from the group consisting of H, $C_{1-5}$ alkyl, $C_{2-5}$ alkenyl, $C_{2-5}$ alkynyl, and $C_{3-6}$ cycloalkyl, each of which may be optionally substituted with one or more, identical or different, substituents R⁷; phenyl optionally substituted with one or more, identical or different, substituents R⁹; and benzyl optionally substituted with one or more, identical or different, substituents R⁹;
R⁶ is selected from the group consisting of $C_{1-5}$ alkyl and $C_{3-5}$ cycloalkyl, each of which may be optionally substituted with one or more, identical or different, substituents R⁷;
R⁷ is independently selected from the group consisting of deuterium and F;
R⁸ is independently selected from the group consisting of deuterium, F and $C_{1-3}$ alkyl optionally substituted with one or more, identical or different, substituents R⁷;

$R^9$ is independently selected from the group consisting of deuterium, methoxy, nitro, cyano, Cl, Br, I and F; and n is an integer 0, 1, 2 or 3; and X is O, S, SO or $SO_2$;

or a pharmaceutically acceptable salt, hydrate, polymorph, tautomer, or solvate thereof.

In another aspect, the disclosure concerns a compound as defined herein for use in treating, ameliorating and/or preventing a neuromuscular disorder, and/or for use in reversing and/or ameliorating a neuromuscular blockade. In yet another aspect, the disclosure concerns a composition comprising a compound as defined herein.

DETAILED DESCRIPTION

Definitions

Figure 1:
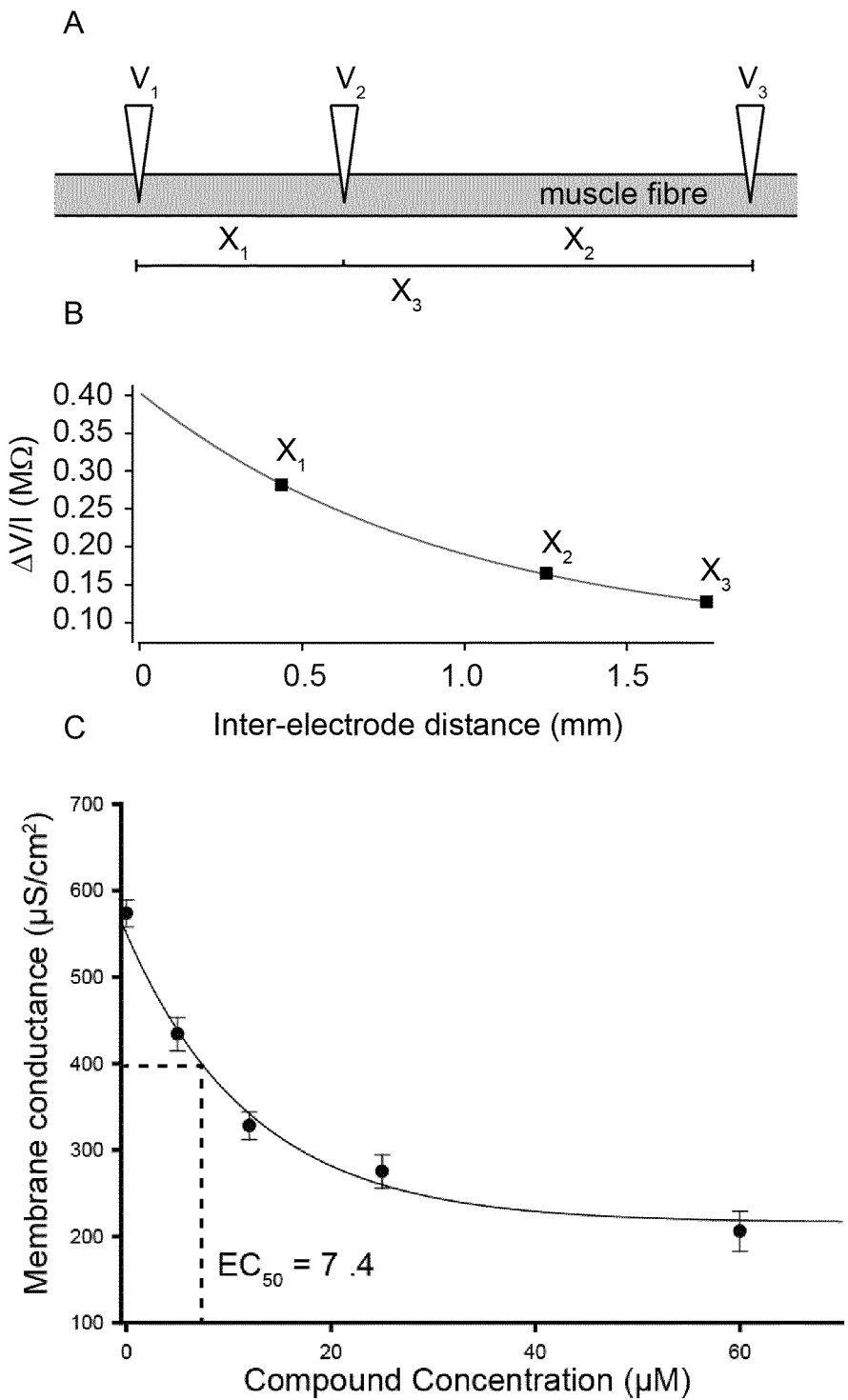
FIG. 1. Panel A shows a schematic representation of the positioning of the three microelectrodes ($V_1$, $V_2$ and $V_3$) when inserted in a single skeletal muscle fibre for $G_m$ determination. Please note that the drawing illustrates only the impaled fibre although it is part of an intact muscle that contains many such fibres. All electrodes recorded the membrane potential of the fibre and the two peripheral electrodes were used to inject current (−30 nA, 50 ms). The electrodes were inserted with known inter-electrode distances ($X_1$, $X_2$ and $X_3$). After insertion, current was passed first via the $V_1$ electrode and then via the $V_3$ electrode. The resulting deflections in the membrane voltage were measured by the other electrodes. The steady state deflections in membrane potential were measured and divided by the magnitude of the injected current (−30 nA) to obtain transfer resistances. These were next plotted against inter-electrode distances, and fitted to an exponential function (Panel B), from which $G_m$ could be calculated using linear cable theory. The approach described in panel A and B, was repeated for several muscle fibres in the muscle during exposure at increasing concentrations of compound A-1, with approx. 10 fibres at each concentration. Average $G_m$ at each concentration was plotted as a function of compound concentration in panel C, and fitted to a 4-parameter sigmoidal function from which the $EC_{50}$ value for the compound was obtained (dashed line)

The terms "$C_{1-3}$ alkyl", "$C_{1-5}$ alkyl" and "$C_{2-5}$ alkyl" refers to a branched or unbranched alkyl group having from one to three, one to five or two to five carbon atoms respectively, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.

The term "$C_{2-5}$ alkenyl" refers to a branched or unbranched alkenyl group having from one to five carbon atoms, two of which are connected by a double bond, including but not limited to ethenyl, propenyl, isopropenyl, butenyl, isobutenyl, pentenyl and isopentenyl.

The term "$C_{2-5}$ alkynyl" refers to a branched or unbranched alkynyl group having from one to five carbon atoms, two of which are connected by a triple bond, including but not limited to ethynyl, prop-1-ynyl, prop-2-ynyl, but-1-ynyl, but-2-ynyl, but-3-ynyl, buta-1,3-diynyl, pent-1-ynyl, pent-2-ynyl, pent-3-ynyl, pent-4-ynyl, penta-2,4-diynyl and penta-1,3-diynyl.

The term "$C_{1-3}$ alkanediyl" refers to an unbranched alkyl group having one to three carbon atoms having the general formula —$C_pH_{2p}$—, wherein p is an integer 1, 2 or 3. Examples of "$C_{1-3}$ alkanediyl" include methylene (—$CH_2$—), ethane-1,2-diyl (—$CH_2CH_2$—) or propane-1,3-diyl (—$CH_2CH_2CH_2$—).

The term "$C_{3-5}$ cycloalkyl" and "$C_{3-6}$ cycloalkyl" refers to a group having three to five or three to six carbon atoms respectively including a monocyclic or bicyclic carbocycle, including but not limited to cyclopropyl, cyclobutyl, cyclopentyl, cyclohexyl, cyclopropylmethyl, cyclopropylethyl, cyclobutylmethyl, cyclobutylethyl and cyclopentylmethyl. Examples of $C_{3-5}$ cycloalkyl wherein one —$CH_2$— is replaced by —O— are oxiran-2-yl, oxetan-2-yl, oxetan-3-yl, oxolan-2-yl and oxolan-3-yl.

The term "half-life" as used herein is the time it takes for the compound to lose one-half of its pharmacologic activity. The term "plasma half-life" is the time that it takes the compound to lose one-half of its pharmacologic activity in the blood plasma.

The term "treatment" refers to the combating of a disease or disorder. "Treatment" or "treating," as used herein, includes any desirable effect on the symptoms or pathology of a disease or condition as described herein, and may include even minimal changes or improvements in one or more measurable markers of the disease or condition being treated. "Treatment" or "treating" does not necessarily indicate complete eradication or cure of the disease or condition, or associated symptoms thereof. In some embodiments, the term "treatment" encompasses amelioration and prevention.

The term "amelioration" refers to moderation in the severity of the symptoms of a disease or condition. Improvement in a patient's condition, or the activity of making an effort to correct, or at least make more acceptable, conditions that are difficult to endure related to patient's conditions is considered "ameliorative" treatment.

The term "prevent" or "preventing" refers to precluding, averting, obviating, forestalling, stopping, or hindering something from happening, especially by advance action.

The term "reversal" or "reversing" refers to the ability of a compound to restore nerve-stimulated force in skeletal muscle exposed either ex vivo or in vivo to a non-depolarizing neuromuscular blocking agent or another pharmaceutical that is able to depress neuromuscular transmission The term "non-depolarizing blockers" refers to pharmaceutical agents that antagonize the activation of acetylcholine receptors at the post-synaptic muscle fibre membrane by blocking the acetylcholine binding site on the receptor. These agents are used to block neuromuscular transmission and induce muscle paralysis in connection with surgery.

The term "ester hydrolysing reagent" refers to a chemical reagent which is capable of converting an ester functional group to a carboxylic acid with elimination of the alcohol moiety of the original ester, including but not limited to acid, base, a fluoride source, $PBr_3$, $PCl_3$ and lipase enzymes.

The term "recovery of force in muscle with neuromuscular dysfunction" refers to the ability of a compound to recover contractile force in nerve-stimulated healthy rat muscle after exposure to submaximal concentration of (115 nM) tubocurarine for 90 mins. Recovery of force is quantified as the percentage of the force prior to tubocurarine that is recovered by the compound.

The term "total membrane conductance ($G_m$)" is the electrophysiological measure of the ability of ions to cross the muscle fibre surface membrane. It reflects the function of ion channels that are active in resting muscle fibres of which ClC-1 is known to contribute around 80% in most animal species.

Compounds

It is within the scope of the present disclosure to provide a compound for use in treating, ameliorating and/or preventing neuromuscular disorders characterized in that the neuromuscular function is reduced. As disclosed herein, inhibition of ClC-1 improves or restores neuromuscular function. The compounds of the present disclosure comprise compounds capable of inhibiting the ClC-1 channel thereby improving or restoring neuromuscular function.

In one aspect, the disclosure concerns a compound of Formula (I):

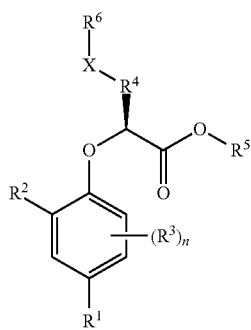

Formula (I)

wherein:
- $R^1$ is selected from the group consisting of F, Cl, Br and I;
- $R^2$ is selected from the group consisting of $C_{2-5}$ alkyl optionally substituted with one or more, identical or different, substituents $R^8$ and $C_{3-5}$ cycloalkyl optionally substituted with one or more, identical or different, substituents $R^8$ and wherein one —$CH_2$— in the $C_{2-5}$ alkyl or $C_{3-5}$ cycloalkyl is optionally replaced by —O—;
- $R^3$ is selected from the group consisting of deuterium, Cl and F;
- $R^4$ is $C_{1-3}$ alkanediyl which may be optionally substituted with one or more, identical or different, substituents $R^8$;
- $R^5$ is selected from the group consisting of H, $C_{1-5}$ alkyl, $C_{2-5}$ alkenyl, $C_{2-5}$ alkynyl, and $C_{3-6}$ cycloalkyl, each of which may be optionally substituted with one or more, identical or different, substituents $R^7$; phenyl optionally substituted with one or more, identical or different, substituents $R^9$; and benzyl optionally substituted with one or more, identical or different, substituents $R^9$;
- $R^6$ is selected from the group consisting of $C_{1-5}$ alkyl and $C_{3-5}$ cycloalkyl, each of which may be optionally substituted with one or more, identical or different, substituents $R^7$;
- $R^7$ is independently selected from the group consisting of deuterium and F;
- $R^8$ is independently selected from the group consisting of deuterium, F and $C_{1-3}$ alkyl optionally substituted with one or more, identical or different, substituents $R^7$;
- $R^9$ is independently selected from the group consisting of deuterium, methoxy, nitro, cyano, Cl, Br, I and F; and
- n is an integer 0, 1, 2 or 3; and
- X is O, S, SO or $SO_2$;

or a pharmaceutically acceptable salt, hydrate, polymorph, tautomer, or solvate thereof.

In one aspect, the disclosure concerns a compound of Formula (I):

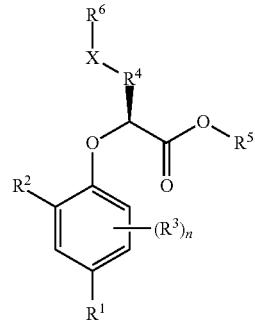

Formula (I)

wherein:
- $R^1$ is selected from the group consisting of F, Cl, Br and I;
- $R^2$ is selected from the group consisting of $C_{2-5}$ alkyl optionally substituted with one or more, identical or different, substituents $R^1$ and $C_{3-5}$ cycloalkyl optionally substituted with one or more, identical or different, substituents $R^7$ and wherein one —$CH_2$— is optionally replaced by —O— of said $C_{2-5}$ alkyl or $C_{3-5}$ cycloalkyl;
- $R^3$ is selected from the group consisting of deuterium and F;
- $R^4$ is $C_{1-3}$ alkanediyl which may be optionally substituted with one or more, identical or different, substituents $R^8$;
- $R^5$ is selected from the group consisting of H, $C_{1-5}$ alkyl, $C_{2-5}$ alkenyl, $C_{2-5}$ alkynyl, $C_{3-6}$ cycloalkyl each of which may be optionally substituted with one or more, identical or different, substituents $R^7$, phenyl optionally substituted with one or more, identical or different, substituents $R^9$ and benzyl optionally substituted with one or more, identical or different, substituents $R^9$;
- $R^8$ is selected from the group consisting of $C_{1-5}$ alkyl and $C_{3-5}$ cycloalkyl each of which may be optionally substituted with one or more, identical or different, substituents $R^7$;
- $R^7$ is independently selected from the group consisting of deuterium and F;
- $R^8$ is independently selected from the group consisting of deuterium, F and $C_{1-3}$ alkyl optionally substituted with one or more, identical or different, substituents $R^7$;

$R^9$ is independently selected from the group consisting of deuterium, methoxy, nitro, cyano, Cl, Br, I and F; and n is an integer 0, 1, 2 or 3; and X is O, S, SO or $SO_2$;

or a pharmaceutically acceptable salt, hydrate, polymorph, tautomer, or solvate thereof.

In one embodiment, $R^1$ is Cl or Br. In one embodiment, $R^1$ is Cl.

In one embodiment, $R^1$ is Br.

In one embodiment, $R^2$ is selected from the group consisting of $C_{2-5}$ alkyl optionally substituted with one or more, identical or different, substituents $R^7$ and $C_{3-5}$ cycloalkyl optionally substituted with one or more, identical or different, substituents $R^7$ and wherein one —$CH_2$— in the $C_{2-5}$ alkyl or $C_{3-5}$ cycloalkyl is optionally replaced by —O—.

In one embodiment, $R^2$ is $C_{2-5}$ alkyl optionally substituted with one or more, identical or different, substituents $R^8$.

In one embodiment, $R^2$ is $C_{3-5}$ cycloalkyl optionally substituted with one or more, identical or different, substituents $R^8$. In one embodiment, $R^2$ is $C_{3-5}$ cycloalkyl. In one embodiment, $R^2$ is cyclopropyl or cyclobutyl, such as cyclopropyl. In one embodiment, $R^2$ is $C_{3-5}$ cycloalkyl substituted with one or more, identical or different, substituents $R^8$.

In one embodiment, $R^2$ is $C_{3-5}$ cycloalkyl substituted with one or more F. In one embodiment, $R^2$ is $C_{3-5}$ cycloalkyl substituted with one or more deuterium. In one embodiment, $R^2$ is cyclopropyl or cyclobutyl, such as cyclopropyl, substituted with one or more deuterium and/or one or more F.

In one embodiment, $R^2$ is $C_{3-5}$ cycloalkyl substituted with $C_{1-3}$ alkyl optionally substituted with one or more, identical or different, substituents $R^7$. In one embodiment, $R^2$ is selected from the group consisting of 1-methylcycloprop-1-yl, 1-ethylcycloprop-1-yl, 1-propylcycloprop-1-yl, (1-methylethyl)cycloprop-1-yl, 1-methylcyclobut-1-yl, 1-ethylcyclobut-1-yl, 1-propylcyclobut-1-yl, (1-methylethyl)cyclobut-1-yl, 1-methylcyclopent-1-yl, 1-ethylcyclopent-1-yl, 1-propylcyclopent-1-yl and (1-methylethyl)cyclopent-1-yl, each of which may be optionally substituted with one or more, identical or different, substituents $R^7$.

In one embodiment, $R^2$ is $C_{3-5}$ cycloalkyl wherein one —$CH_2$— is replaced by —O— and the $C_{3-5}$ cycloalkyl is optionally substituted with one or more, identical or different, substituents $R^8$. In one embodiment, $R^2$ is oxiran-2-yl, oxetan-2-yl, oxetan-3-yl, oxolan-2-yl or oxolan-3-yl.

In one embodiment, $R^2$ is $C_{2-5}$ alkyl optionally substituted with one or more, identical or different, substituents $R^7$. In one embodiment, $R^2$ is $C_{2-5}$ alkyl, preferably isopropyl. In one embodiment, $R^2$ is $C_{2-5}$ alkyl substituted with one or more, identical or different, substituents $R^7$. In one embodiment, $R^2$ is isopropyl substituted with one or more, identical or different, substituents $R^7$.

In one embodiment, $R^2$ is $C_{3-5}$ cycloalkyl optionally substituted with one or more, identical or different, substituents $R^7$. In one embodiment, $R^2$ is $C_{3-5}$ cycloalkyl. In one embodiment, $R^2$ is cyclopropyl or cyclobutyl, preferably cyclopropyl. In one embodiment, $R^2$ is $C_{3-5}$ cycloalkyl substituted with one or more, identical or different, substituents $R^7$. In one embodiment, $R^2$ is $C_{3-5}$ cycloalkyl substituted with one or more F. In one embodiment, $R^2$ is $C_{3-5}$ cycloalkyl substituted with one or more deuterium. In one embodiment, $R^2$ is cyclopropyl or cyclobutyl, preferably cyclopropyl, substituted with one or more deuterium and/or one or more F.

In one embodiment, $R^2$ is $C_{3-5}$ cycloalkyl wherein one —$CH_2$— is replaced by —O-optionally substituted with one or more, identical or different, substituents $R^7$. In one embodiment, $R^2$ is oxiran-2-yl, oxetan-2-yl, oxetan-3-yl, oxolan-2-yl or oxolan-3-yl.

In one embodiment, $R^3$ is deuterium. In one embodiment, $R^3$ is F. In one embodiment, $R^3$ is deuterium or F. In one embodiment, $R^3$ is Cl.

In one embodiment, $R^4$ is $C_{1-3}$ alkanediyl, such as methylene (—$CH_2$—), ethane-1,2-diyl (—$CH_2CH_2$—) or propane-1,3-diyl (—$CH_2CH_2CH_2$—) each of which may be optionally substituted with one or more, identical or different, substituents $R^8$. In one embodiment, $R^4$ is $C_{1-3}$ alkanediyl, such as methylene, ethane-1,2-diyl or propane-1,3-diyl each of which is substituted with one or more, identical or different, substituents $R^8$. In one embodiment, $R^4$ is $C_{1-3}$ alkanediyl, such as methylene, ethane-1,2-diyl or propane-1,3-diyl, preferably methylene.

In one embodiment, $R^5$ is H. In one embodiment, $R^5$ is $C_{1-5}$ alkyl optionally substituted with one or more, identical or different, substituents $R^7$. In one embodiment, $R^5$ is $C_{3-3}$ cycloalkyl optionally substituted with one or more, identical or different, substituents $R^7$.

In one embodiment, $R^5$ is phenyl optionally substituted with one or more, identical or different, substituents $R^9$. In one embodiment, $R^5$ is benzyl optionally substituted with one or more, identical or different, substituents $R^9$.

In one embodiment, $R^6$ is $C_{1-5}$ alkyl optionally substituted with one or more, identical or different, substituents $R^7$. In one embodiment, $R^6$ is $C_{3-5}$ cycloalkyl optionally substituted with one or more, identical or different, substituents $R^7$. In one embodiment, $R^6$ is $C_{1-5}$ alkyl substituted with one or more, identical or different, substituents $R^7$. In one embodiment, $C_{3-5}$ cycloalkyl substituted with one or more, identical or different, substituents $R^7$. In one embodiment, $R^6$ is $C_{1-3}$ alkyl optionally substituted with one or more, identical or different, substituents $R^7$. In one embodiment, $R^6$ is methyl optionally substituted with one or more, identical or different, substituents $R^7$. In one embodiment, $R^6$ is ethyl optionally substituted with one or more, identical or different, substituents $R^7$. In one embodiment, $R^6$ is n-propyl optionally substituted with one or more, identical or different, substituents $R^7$. In one embodiment, $R^6$ is isopropyl optionally substituted with one or more, identical or different, substituents $R^7$. In one embodiment, cyclopropyl optionally substituted with one or more, identical or different, substituents $R^7$.

In one embodiment, $R^7$ is deuterium. In one embodiment, $R^7$ is F.

In one embodiment, $R^8$ is deuterium. In one embodiment, $R^8$ is F. In one embodiment, $R^6$ is $C_{1-3}$ alkyl optionally substituted with one or more, identical or different, substituents $R^7$.

In one embodiment, n is 0. In one embodiment, n is 1. In one embodiment, n is 2. In one embodiment, n is 3.

In one embodiment, X is O. In one embodiment, X is S. In one embodiment, X is SO. In one embodiment, X is $SO_2$. In one embodiment, X is O or S.

In one embodiment, $R^1$ is Cl or Br, $R^2$ is $C_{3-5}$ cycloalkyl optionally substituted with one or more, identical or different, substituents $R^8$, $R^4$ is methylene, $R^5$ is H, $R^6$ is $C_{1-5}$ alkyl optionally substituted with one or more, identical or different, substituents $R^8$ and X is O.

In one embodiment, $R^1$ is Cl or Br, $R^2$ is $C_{2-5}$ alkyl optionally substituted with one or more, identical or different, substituents $R^8$, $R^4$ is methylene, $R^5$ is H, $R^6$ is $C_{1-5}$ alkyl optionally substituted with one or more, identical or different, substituents $R^8$ and X is O.

In one embodiment, $R^1$ is Cl or Br, $R^2$ is $C_{3-5}$ cycloalkyl optionally substituted with one or more, identical or different, substituents $R^8$, $R^4$ is methylene, $R^5$ is H, $R^6$ is $C_{3-5}$ cycloalkyl optionally substituted with one or more, identical or different, substituents $R^8$ and X is O.

In one embodiment, $R^1$ is Cl or Br, $R^2$ is $C_{2-5}$ alkyl optionally substituted with one or more, identical or different, substituents $R^8$, $R^4$ is methylene, $R^5$ is H, $R^6$ is $C_{3-5}$ cycloalkyl optionally substituted with one or more, identical or different, substituents $R^8$ and X is O.

In one embodiment, $R^1$ is Cl or Br, $R^2$ is $C_{3-5}$ cycloalkyl optionally substituted with one or more, identical or different, substituents $R^8$, $R^4$ is methylene, $R^5$ is H, $R^6$ is $C_{1-5}$ alkyl optionally substituted with one or more, identical or different, substituents $R^8$ and X is S.

In one embodiment, $R^1$ is Cl or Br, $R^2$ is $C_{2-5}$ alkyl optionally substituted with one or more, identical or different, substituents $R^8$, $R^4$ is methylene, $R^5$ is H, $R^6$ is $C_{1-5}$ alkyl optionally substituted with one or more, identical or different, substituents $R^8$ and X is S.

In one embodiment, $R^1$ is Cl or Br, $R^2$ is $C_{3-5}$ cycloalkyl optionally substituted with one or more, identical or different, substituents $R^8$, $R^4$ is methylene, $R^5$ is H, $R^6$ is $C_{3-5}$ cycloalkyl optionally substituted with one or more, identical or different, substituents $R^8$ and X is S.

In one embodiment, $R^1$ is Cl or Br, $R^2$ is $C_{2-5}$ alkyl optionally substituted with one or more, identical or different, substituents $R^8$, $R^4$ is methylene, $R^5$ is H, $R^6$ is $C_{3-5}$ cycloalkyl optionally substituted with one or more, identical or different, substituents $R^8$ and X is S.

In one embodiment, $R^1$ is Cl or Br, $R^2$ is $C_{3-5}$ cycloalkyl optionally substituted with one or more, identical or different, substituents $R^1$, $R^4$ is methylene, $R^5$ is H, $R^6$ is $C_{1-5}$ alkyl optionally substituted with one or more, identical or different, substituents $R^7$ and X is O.

In one embodiment, $R^1$ is Cl or Br, $R^2$ is $C_{2-5}$ alkyl optionally substituted with one or more, identical or different, substituents $R^7$, $R^4$ is methylene, $R^5$ is H, $R^6$ is $C_{1-5}$ alkyl optionally substituted with one or more, identical or different, substituents $R^7$ and X is O.

In one embodiment, $R^1$ is Cl or Br, $R^2$ is $C_{3-5}$ cycloalkyl optionally substituted with one or more, identical or different, substituents $R^7$, $R^4$ is methylene, $R^5$ is H, $R^6$ is $C_{3-5}$ cycloalkyl optionally substituted with one or more, identical or different, substituents $R^7$ and X is O.

In one embodiment, $R^1$ is Cl or Br, $R^2$ is $C_{2-5}$ alkyl optionally substituted with one or more, identical or different, substituents $R^7$, $R^4$ is methylene, $R^5$ is H, $R^6$ is $C_{3-5}$ cycloalkyl optionally substituted with one or more, identical or different, substituents $R^7$ and X is O.

In one embodiment, $R^1$ is Cl or Br, $R^2$ is $C_{3-5}$ cycloalkyl optionally substituted with one or more, identical or different, substituents $R^1$, $R^4$ is methylene, $R^5$ is H, $R^6$ is $C_{1-5}$ alkyl optionally substituted with one or more, identical or different, substituents $R^7$ and X is S.

In one embodiment, $R^1$ is Cl or Br, $R^2$ is $C_{2-5}$ alkyl optionally substituted with one or more, identical or different, substituents $R^7$, $R^4$ is methylene, $R^6$ is H, $R^6$ is $C_{1-5}$ alkyl optionally substituted with one or more, identical or different, substituents $R^7$ and X is S.

In one embodiment, $R^1$ is Cl or Br, $R^2$ is $C_{3-5}$ cycloalkyl optionally substituted with one or more, identical or different, substituents $R^7$, $R^4$ is methylene, $R^5$ is H, $R^6$ is $C_{3-5}$ cycloalkyl optionally substituted with one or more, identical or different, substituents $R^7$ and X is S.

In one embodiment, $R^1$ is Cl or Br, $R^2$ is $C_{2-5}$ alkyl optionally substituted with one or more, identical or different, substituents $R^7$, $R^4$ is methylene, $R^5$ is H, $R^6$ is $C_{3-5}$ cycloalkyl optionally substituted with one or more, identical or different, substituents $R^7$ and X is S.

In one embodiment, the $EC_{50}$ of the compound is <50 µM, such as <40 µM, such as <30 µM, such as <20 µM, such as <15 µM, such as <10 µM, and such as <5 µM. In one embodiment, the recovery of force in muscles with neuromuscular dysfunction is >5%, for example >10%, for example >15%, for example >20%, for example >25%, for example >30% and for example >35%.

It should be understood in the context of the present application that the phrase 'wherein one —$CH_2$— in the $C_{2-5}$ alkyl or $C_{3-5}$ cycloalkyl is optionally replaced by —O—' is identical in meaning to the phrase 'wherein one —$CH_2$— is optionally replaced by —O— of said $C_{2-5}$ alkyl or $C_{3-5}$ cycloalkyl'.

In one aspect, the disclosure concerns a compound of Formula (I):

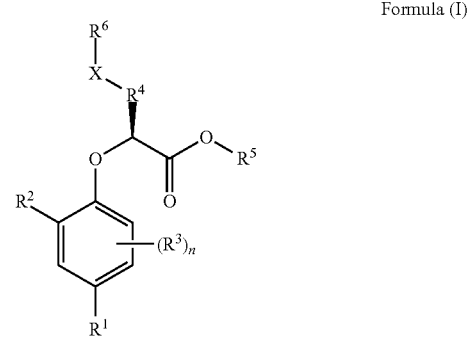

Formula (I)

wherein:
R$^1$ is selected from the group consisting of F, Cl, Br and I;

R$^2$ is selected from the group consisting of $C_{2-5}$ alkyl and $C_{3-5}$ cycloalkyl, each of which may be optionally substituted with one or more, identical or different, substituents R$^8$;

R$^3$ is selected from the group consisting of deuterium and F;

R$^4$ is $C_{1-3}$ alkanediyl which may be optionally substituted with one or more, identical or different, substituents R$^8$;

R$^5$ is selected from the group consisting of H, $C_{1-5}$ alkyl, $C_{2-5}$ alkenyl, $C_{2-5}$ alkynyl, and $C_{3-6}$ cycloalkyl, each of which may be optionally substituted with one or more, identical or different, substituents R$^7$; phenyl optionally substituted with one or more, identical or different, substituents R$^9$; and benzyl optionally substituted with one or more, identical or different, substituents R$^9$;

R$^8$ is selected from the group consisting of $C_{1-5}$ alkyl and $C_{3-5}$ cycloalkyl, each of which may be optionally substituted with one or more, identical or different, substituents R$^7$;

R$^7$ is independently selected from the group consisting of deuterium and F;

R$^8$ is independently selected from the group consisting of deuterium, F and $C_{1-3}$ alkyl optionally substituted with one or more, identical or different, substituents R$^7$;

R$^9$ is independently selected from the group consisting of deuterium, methoxy, nitro, cyano, Cl, Br, I and F; and n is an integer 0, 1, 2 or 3; and
X is O or S;
or a pharmaceutically acceptable salt, hydrate, polymorph, tautomer, or solvate thereof.

In one embodiment, the disclosure concerns a compound of Formula (II):

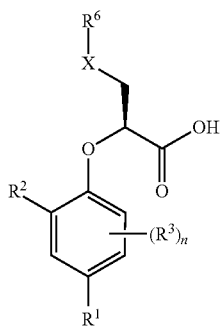

Formula (II)

wherein:
R$^1$ is selected from the group consisting of Cl and Br;
R$^2$ is C$_{3-5}$ cycloalkyl optionally substituted with one or more, identical or different, substituents R$^8$;
R$^3$ is selected from the group consisting of deuterium and F;
R$^8$ is selected from the group consisting of C$_{1-5}$ alkyl and C$_{3-5}$ cycloalkyl, each of which may be optionally substituted with one or more, identical or different, substituents R$^7$;
R$^7$ is independently selected from the group consisting of deuterium and F;
R$^8$ is independently selected from the group consisting of deuterium, F and C$_{1-3}$ alkyl optionally substituted with one or more, identical or different, substituents R$^7$;
n is an integer 0, 1, 2 or 3; and
X is O or S;
or a pharmaceutically acceptable salt, hydrate, polymorph, tautomer, or solvate thereof.

In one embodiment, the disclosure concerns a compound of Formula (II):

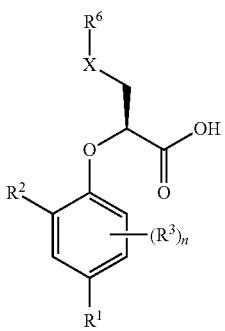

Formula (II)

wherein:
R$^1$ is selected from the group consisting of Cl and Br;
R$^2$ is selected from the group consisting of C$_{2-5}$ alkyl and C$_{3-5}$ cycloalkyl each of which may be optionally substituted with one or more, identical or different, substituents R$^7$;
R$^3$ is selected from the group consisting of deuterium and F;
R$^6$ is selected from the group consisting of C$_{1-5}$ alkyl and C$_{3-5}$ cycloalkyl each of which may be optionally substituted with one or more, identical or different, substituents R$^7$;
R$^7$ is independently selected from the group consisting of deuterium and F;
n is an integer 0, 1, 2 or 3; and
X is O or S;
or a pharmaceutically acceptable salt, hydrate, polymorph, tautomer, or solvate thereof.

In one embodiment, the disclosure concerns a compound of Formula (III):

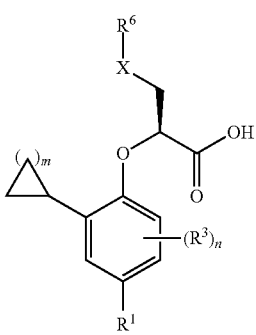

Formula (III)

wherein:
R$^1$ is selected from the group consisting of Cl and Br;
R$^3$ is selected from the group consisting of deuterium and F;
R$^6$ is selected from the group consisting of C$_{1-5}$ alkyl and C$_{3-5}$ cycloalkyl each of which may be optionally substituted with one or more, identical or different, substituents R$^7$;
R$^7$ is independently selected from the group consisting of deuterium and F;
m is an integer 1 or 2;
n is an integer 0, 1, 2 or 3; and
X is O or S;
or a pharmaceutically acceptable salt, hydrate, polymorph, tautomer, or solvate thereof.

In one embodiment, m is 1. In one embodiment, m is 2.

In one embodiment, the compound is selected from the list consisting of
(2S)-2-(4-bromo-2-cyclopropylphenoxy)-3-methoxypropanoic acid;
(2S)-2-(4-bromo-2-cyclopropylphenoxy)-3-ethoxypropanoic acid;
(2S)-2-(4-bromo-2-cyclopropyl-5-fluorophenoxy)-3-methoxypropanoic acid;
(2S)-2-[4-bromo-2-(1-ethylcyclopropyl)phenoxy]-3-methoxypropanoic acid;
(2S)-2-(4-bromo-2-cyclopropylphenoxy)-3-(difluoromethoxy)propanoic acid;
(2S)-2-(4-chloro-2-cyclopropylphenoxy)-3-methoxypropanoic acid;
(2S)-2-(4-bromo-2-cyclopropylphenoxy)-3-methoxybutanoic acid;
(2S,3S)-2-(4-chloro-2-cyclopropyl-5-fluorophenoxy)-3-methoxypropanoic acid;
(2R)-2-(4-bromo-2-cyclobutylphenoxy)-3-(methylsulfanyl)propanoic acid;

(2S)-2-(4-bromo-2-cyclobutylphenoxy)-3-methoxypropanoic acid;
(2S)-2-(4-bromo-2-cyclopropylphenoxy)-4-methoxybutanoic acid;
(2R)-2-(4-bromo-2-cyclopropylphenoxy)-3-(methylsulfanyl)propanoic acid; and
(2S)-2-[4-bromo-2-(propan-2-yl)phenoxy]-3-methoxypropanoic acid.

Methods of Treatment

In one aspect, the disclosure relates to the use of compounds of Formula (I), Formula (II) and/or Formula (III) in treating, ameliorating and/or preventing a neuromuscular disorder. In one aspect, the disclosure relates to the use of compounds of Formula (I), Formula (II) and/or Formula (III) in reversing and/or ameliorating a neuromuscular blockade. Thus, in one aspect, the disclosure relates to a compound of Formula (I):

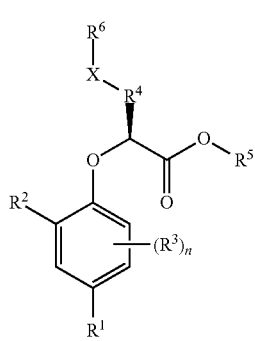

Formula (I)

wherein $R^1$ to $R^9$, n and X are defined as disclosed herein,
or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one aspect, the disclosure concerns a compound of Formula (I):

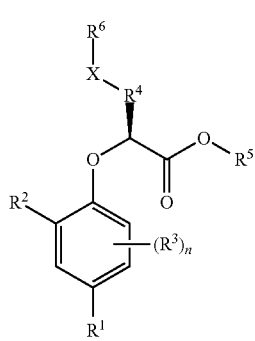

Formula (I)

wherein:
$R^1$ is selected from the group consisting of F, Cl, Br and I;
$R^2$ is selected from the group consisting of $C_{2-5}$ alkyl optionally substituted with one or more, identical or different, substituents $R^8$ and $C_{3-5}$ cycloalkyl optionally substituted with one or more, identical or different, substituents $R^8$ and wherein one —$CH_2$— in the $C_{2-5}$ alkyl or $C_{3-5}$ cycloalkyl is optionally replaced by —O—;
$R^3$ is selected from the group consisting of deuterium, Cl and F;
$R^4$ is $C_{3-6}$ alkanediyl which may be optionally substituted with one or more, identical or different, substituents $R^8$;
$R^5$ is selected from the group consisting of H, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$; phenyl optionally substituted with one or more, identical or different, substituents $R^9$; and benzyl optionally substituted with one or more, identical or different, substituents $R^9$;
$R^6$ is selected from the group consisting of $C_{1-5}$ alkyl and $C_{3-5}$ cycloalkyl, each of which may be optionally substituted with one or more, identical or different, substituents $R^7$;
$R^7$ is independently selected from the group consisting of deuterium and F;
$R^8$ is independently selected from the group consisting of deuterium, F and $C_{1-3}$ alkyl optionally substituted with one or more, identical or different, substituents $R^7$;
$R^9$ is independently selected from the group consisting of deuterium, methoxy, nitro, cyano, Cl, Br, I and F; and
n is an integer 0, 1, 2 or 3; and
X is O, S, SO or $SO_2$;
or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one aspect, the disclosure concerns a compound of Formula (I):

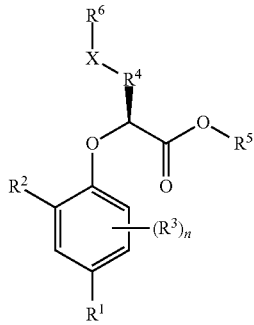

Formula (I)

wherein:
$R^1$ is selected from the group consisting of F, Cl, Br and I;
$R^2$ is selected from the group consisting of $C_{2-5}$ alkyl optionally substituted with one or more, identical or different, substituents $R^7$ and $C_{3-5}$ cycloalkyl optionally substituted with one or more, identical or different, substituents $R^7$ and wherein one —$CH_2$— in the $C_{2-5}$ alkyl or $C_{3-5}$ cycloalkyl is optionally replaced by —O—;
$R^3$ is selected from the group consisting of deuterium and F;
$R^4$ is $C_{1-3}$ alkanediyl which may be optionally substituted with one or more, identical or different, substituents $R^8$;

$R^5$ is selected from the group consisting of H, $C_{1-5}$ alkyl, $C_{2-5}$ alkenyl, $C_{2-5}$ alkynyl, and $C_{3-6}$ cycloalkyl, each of which may be optionally substituted with one or more, identical or different, substituents $R^7$; phenyl optionally substituted with one or more, identical or different, substituents $R^9$; and benzyl optionally substituted with one or more, identical or different, substituents $R^9$;

$R^6$ is selected from the group consisting of $C_{1-5}$ alkyl and $C_{3-5}$ cycloalkyl, each of which may be optionally substituted with one or more, identical or different, substituents $R^7$;

$R^7$ is independently selected from the group consisting of deuterium and F;

$R^8$ is independently selected from the group consisting of deuterium, F and $C_{1-3}$ alkyl optionally substituted with one or more, identical or different, substituents $R^7$;

$R^9$ is independently selected from the group consisting of deuterium, methoxy, nitro, cyano, Cl, Br, I and F; and n is an integer 0, 1, 2 or 3; and X is O, S, SO or $SO_2$;

or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one aspect, the disclosure concerns a compound of Formula (I):

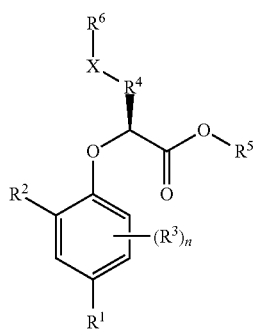

Formula (I)

wherein:

$R^1$ is selected from the group consisting of F, Cl, Br and I;

$R^2$ is selected from the group consisting of $C_{2-5}$ alkyl and $C_{3-5}$ cycloalkyl, each of which may be optionally substituted with one or more, identical or different, substituents $R^8$;

$R^3$ is selected from the group consisting of deuterium and F;

$R^4$ is $C_{1-3}$ alkanediyl which may be optionally substituted with one or more, identical or different, substituents $R^8$;

$R^5$ is selected from the group consisting of H, $C_{1-5}$ alkyl, $C_{2-5}$ alkenyl, $C_{2-5}$ alkynyl, and $C_{3-8}$ cycloalkyl, each of which may be optionally substituted with one or more, identical or different, substituents $R^7$; phenyl optionally substituted with one or more, identical or different, substituents $R^9$; and benzyl optionally substituted with one or more, identical or different, substituents $R^9$;

$R^6$ is selected from the group consisting of $C_{1-5}$ alkyl and $C_{3-5}$ cycloalkyl, each of which may be optionally substituted with one or more, identical or different, substituents $R^7$;

$R^7$ is independently selected from the group consisting of deuterium and F;

$R^8$ is independently selected from the group consisting of deuterium, F and $C_{1-3}$ alkyl optionally substituted with one or more, identical or different, substituents $R^7$;

$R^9$ is independently selected from the group consisting of deuterium, methoxy, nitro, cyano, Cl, Br, I and F; and n is an integer 0, 1, 2 or 3; and X is O or S;

or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the disclosure concerns a compound of Formula (II):

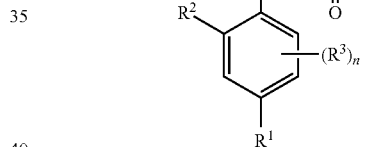

Formula (II)

wherein:

$R^1$ is selected from the group consisting of Cl and Br;

$R^2$ is $C_{3-5}$ cycloalkyl optionally substituted with one or more, identical or different, substituents $R^8$;

$R^3$ is selected from the group consisting of deuterium and F;

$R^6$ is selected from the group consisting of $C_{1-5}$ alkyl and $C_{3-5}$ cycloalkyl, each of which may be optionally substituted with one or more, identical or different, substituents $R^7$;

$R^7$ is independently selected from the group consisting of deuterium and F;

$R^8$ is independently selected from the group consisting of deuterium, F and $C_{1-3}$ alkyl optionally substituted with one or more, identical or different, substituents $R^7$;

n is an integer 0, 1, 2 or 3; and

X is O or S;

or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the disclosure concerns a compound of Formula (II):

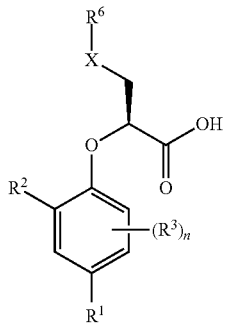

Formula (II)

wherein:
R$^1$ is selected from the group consisting of Cl and Br;
R$^2$ is selected from the group consisting of C$_{2-5}$ alkyl and C$_{3-5}$ cycloalkyl each of which may be optionally substituted with one or more, identical or different, substituents R$^7$;
R$^3$ is selected from the group consisting of deuterium and F;
R$^6$ is selected from the group consisting of C$_{1-5}$ alkyl and C$_{3-5}$ cycloalkyl each of which may be optionally substituted with one or more, identical or different, substituents R$^7$;
R$^7$ is independently selected from the group consisting of deuterium and F;
n is an integer 0, 1, 2 or 3; and
X is O or S;
or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the disclosure concerns a compound of Formula (III):

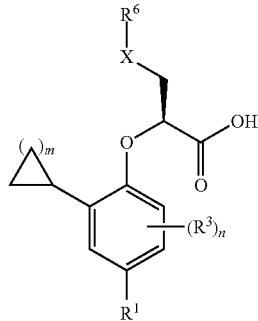

Formula (III)

wherein:
R$^1$ is selected from the group consisting of Cl and Br;
R$^3$ is selected from the group consisting of deuterium and F;
R$^6$ is selected from the group consisting of C$_{1-5}$ alkyl and C$_{3-5}$ cycloalkyl each of which may be optionally substituted with one or more, identical or different, substituents R$^1$;
R$^7$ is independently selected from the group consisting of deuterium and F;
m is an integer 1 or 2;
n is an integer 0, 1, 2 or 3; and
X is O or S;
or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the compound for use in treating, ameliorating and/or preventing a neuromuscular disorder, and/or for use in reversing and/or ameliorating a neuromuscular blockade is selected from the list consisting of
(2S)-2-(4-bromo-2-cyclopropylphenoxy)-3-methoxypropanoic acid;
(2S)-2-(4-bromo-2-cyclopropylphenoxy)-3-ethoxypropanoic acid;
(2S)-2-(4-bromo-2-cyclopropyl-5-fluorophenoxy)-3-methoxypropanoic acid;
(2S)-2-[4-bromo-2-(1-ethylcyclopropyl)phenoxy]-3-methoxypropanoic acid;
(2S)-2-(4-bromo-2-cyclopropylphenoxy)-3-(difluoromethoxy)propanoic acid;
(2S)-2-(4-chloro-2-cyclopropylphenoxy)-3-methoxypropanoic acid:
(2S)-2-(4-bromo-2-cyclopropylphenoxy)-3-methoxybutanoic acid;
(2S,3S)-2-(4-chloro-2-cyclopropyl-5-fluorophenoxy)-3-methoxypropanoic acid;
(2R)-2-(4-bromo-2-cyclobutylphenoxy)-3-(methylsulfanyl)propanoic acid;
(2S)-2-(4-bromo-2-cyclobutylphenoxy)-3-methoxypropanoic acid;
(2S)-2-(4-bromo-2-cyclopropylphenoxy)-4-methoxybutanoic acid;
(2R)-2-(4-bromo-2-cyclopropylphenoxy)-3-(methylsulfanyl)propanoic acid; and
(2S)-2-[4-bromo-2-(propan-2-yl)phenoxy]-3-methoxypropanoic acid.

In certain embodiments, the compound or the compound for use according to the present disclosure can have >90% enantiomeric excess. In certain embodiments, the compound or the compound for use according to the present disclosure can have >95% e.e.

In one embodiment, the compound or the compound for use according to the present disclosure has been modified in order to increase its half-life when administered to a patient, in particular its plasma half-life.

In one embodiment, the compound or the compound for use according to the present disclosure further comprises a moiety conjugated to said compound, thus generating a moiety-conjugated compound. In one embodiment, said moiety-conjugated compound has a plasma and/or serum half-life being longer than the plasma and/or serum half-life of the non-moiety conjugated compound.

In one embodiment, the moiety conjugated to the compound or compound for use according to the present disclosure, is one or more type(s) of moieties selected from the group consisting of albumin, fatty acids, polyethylene glycol (PEG), acylation groups, antibodies and antibody fragments.

Neuromuscular Disorders

The compound or compound for use of the present disclosure is used for treating, ameliorating and/or preventing a neuromuscular disorder, or reversing neuromuscular blockade caused by non-depolarizing neuromuscular blocker or antibiotic agent.

The inventors of the present disclosure have shown that inhibition of ClC-1 channels strengthens neuromuscular transmission. ClC-1 function may therefore contribute to muscle weakness in conditions of compromised neuromuscular transmission.

Thus, in one embodiment of the present disclosure, the compound or the compound for use as described herein inhibits ClC-1 channels. Thus, it is appreciated that compounds and/or compounds for use of Formula (I) inhibit ClC-1 channels.

The neuromuscular disorder may also include neuromuscular dysfunctions.

Neuromuscular disorders include for example disorders with symptoms of muscle weakness and fatigue. Such disorders may include conditions with reduced neuromuscular transmission safety factor. In one embodiment the neuromuscular disorders are motor neuron disorders. Motor neuron disorders are disorders with reduced safety in the neuromuscular transmission. In one embodiment motor neuron disorders are selected from the group consisting of amyotrophic lateral sclerosis (ALS) (Killian J M, Wilfong A A, Burnett L, Appel S H, Boland D. Decremental motor responses to repetitive nerve stimulation in ALS. *Muscle Nerve*, 1994, 17, 747-754), spinal muscular atrophy (SMA) (Wadman R I, Vrancken A F, van den Berg L H, van der Pol W L. Dysfunction of the neuromuscular junction in spinal muscular atrophy types 2 and 3. *Neurology*, 2012, 79, 2050-2055), Charcot-Marie Tooth disease (Bansagi B, Griffin H, Whittaker R G, Antoniadi T, Evangelista T, Miller J, Greenslade M, Forester N, Duff J, Bradshaw A, Kleinle S, Boczonadi V, Steele H, Ramesh V, Franko E, Pyle A, Lochmüller H, Chinnery P F, Horvath R. Genetic heterogeneity of motor neuropathies. *Neurology*, 2017, 28; 88(13): 1226-1234), X-linked spinal and bulbar muscular atrophy (Yamada, M., Inaba, A., Shiojiri, T. X-linked spinal and bulbar muscular atrophy with myasthenic symptoms. *Journal of the Neurological Sciences*, 1997, 146, 183-185), Kennedy's disorder (Stevic, Z., Peric, S., Pavlovic, S., Basta, I., Lavrnic, D., Myasthenic symptoms in a patient with Kennedy's disorder. *Acta Neurologica Belgica*, 2014, 114, 71-73), multifocal motor neuropathy (Roberts, M., Willison, H. J., Vincent, A., Newsom-Davis, J. Multifocal motor neuropathy human sera block distal motor nerve conduction in mice. Ann Neurol. 1995, 38, 111-118), Guillain-Barré syndrome (Ansar, V., Valadi, N. *Guillain-Barré Syndrome Prim. Care*, 2015, 42, 189-193; poliomyelitis (Trojan, D. A., Gendron, D., Cashman, N. R. Electrophysiology and electrodiagnosis of the post-polio motor unit. Orthopedics, 1991, 14, 1353-1361, and Birk T. J. Poliomyelitis and the post-polio syndrome: exercise capacities and adaptation—current research, future directions, and widespread applicability. *Med. Sci. Sports Exerc.*, 1993, 25, 466-472), post-polio syndrome (Garcia, C. C., Potian, J. G., Hognason, K., Thyagarajan, B., Sultatos, L. G., Souayah, N., Routh, V. H., McArdle, J. J. Acetylcholinesterase deficiency contributes to neuromuscular junction dysfunction in type 1 diabetic neuropathy. *Am. J. Physiol. Endocrinol. Metab.*, 2012, 15, E551-561) and sarcopenia (Gilmore K. J., Morat T., Doherty T. J., Rice C. L., Motor unit number estimation and neuromuscular fidelity in 3 stages of sarcopenia. 2017, 55(5):676-684).

Thus, in one preferred embodiment of the present disclosure the neuromuscular disorder is amyotrophic lateral sclerosis (ALS). In another preferred embodiment the neuromuscular disorder is spinal muscular atrophy (SMA). In another preferred embodiment the neuromuscular disorder is Charcot-Marie tooth disease (CMT). In another preferred embodiment the neuromuscular disorder is sarcopenia. In yet another preferred embodiment, the neuromuscular disorder is critical illness myopathy (CIM).

As stated above the neuromuscular disorders include for example disorders with symptoms of muscle weakness and fatigue. Such disorder may for example include diabetes (Burton, A. Take your pyridostigmine: that's an (ethical?) order! *Lancet Neurol.*, 2003, 2, 268).

In one embodiment the compound or the compound for use of the present disclosure is used to prevent neuromuscular disorder. The compound or the compound for use may for example be used prophylactically or as a treatment against nerve gas that is known to cause symptoms of muscle weakness and fatigue (Kawamura, Y., Kihara, M., Nishimoto, K., Taki, M. Efficacy of a half dose of oral pyridostigmine in the treatment of chronic fatigue syndrome: three case reports. *Pathophysiology*, 2003, 9, 189-194). In one embodiment the compound or the compound for use of the present disclosure is used in the treatment of botulism poisoning (Sellin, L. C., The action of botulinum toxin at the neuromuscular junction, *Med Biol.*, 1981, 59, 11-20). In one disclosure, the compound or the compound for use of the present disclosure is used in the treatment of snake bites (Silva A., Maduwage K., Buckley N. A., Lalloo D. G., de Silva H. J., Isbister G. K., Antivenom for snake venom-induced neuromuscular paralysis, Cochrane Database of Systematic Reviews, 2017, 3, Art. No.: CD012604).

In another embodiment the neuromuscular disorders is chronic fatigue syndrome. Chronic fatigue syndrome (CFS) (Fletcher, S. N., Kennedy, D. D., Ghosh, I. R., Misra, V. P., Kiff, K., Coakley, J. H., Hinds, C. J. Persistent neuromuscular and neurophysiologic abnormalities in long-term survivors of prolonged critical illness. *Crit. Care Med.* 2003, 31, 1012-1016) is the common name for a medical condition characterized by debilitating symptoms, including fatigue that lasts for a minimum of six months in adults. CFS may also be referred to as systemic exertion intolerance disorder (SEID), myalgic encephalomyelitis (ME), post-viral fatigue syndrome (PVFS), chronic fatigue immune dysfunction syndrome (CFIDS), or by several other terms. Symptoms of CFS include malaise after exertion; unrefreshing sleep, widespread muscle and joint pain, physical exhaustion, and muscle weakness.

In another embodiment the neuromuscular disorder is myotubular myopathy (Dowling, J. J. et al, Myotubular myopathy and the neuromuscular junction:
a novel therapeutic approach from mouse models, Disease Models & Mechanisms, 2012, 5, 852-859). In another embodiment the neuromuscular disorder is Duchenne muscular dystrophy (van der Pijl, M. M. et al, Characterization of neuromuscular synapse function abnormalities in multiple Duchenne muscular dystrophy mouse models, European Journal of Neuroscience, 2016, 43, 1623-1635.

In a further embodiment the neuromuscular disorder is a critical illness polyneuropathy (Angelini C. Spectrum of metabolic myopathies. *Biochim. Biophys. Acta.*, 2015, 1852, 615-621) or CIM (Latronico, N., Bolton, C. F. Critical illness polyneuropathy and myopathy: a major cause of muscle weakness and paralysis. *Lancet Neurol.* 2011, 10, 931-941). Critical illness polyneuropathy and CIM are overlapping syndromes of widespread muscle weakness and neurological dysfunction developing in critically ill patients.

The neuromuscular disorder may also include metabolic myopathy (Milone, M., Wong, L. J. Diagnosis of mitochondrial myopathies. Mol. Genet. Metab., 2013, 110, 35-41) and mitochondrial myopathy (Srivastava, A., Hunter, J. M. Reversal of neuromuscular block. *Br. J. Anaesth.* 2009, 103, 115-129). Metabolic myopathies result from defects in biochemical metabolism that primarily affects muscle. These may include glycogen storage disorders, lipid storage disorder and 3-phosphocreatine storage disorder. Mitochondrial myopathy is a type of myopathy associated with mitochondrial disorder. Symptoms of mitochondrial myopathies include muscular and neurological problems such as muscle weakness, exercise intolerance, hearing loss and trouble with balance and coordination.

In another embodiment the neuromuscular disorder is periodic paralysis, in particular hypokalemic periodic paralysis which is a disorder of skeletal muscle excitability that presents with recurrent episodes of weakness, often triggered by exercise, stress, or carbohydrate-rich meals (Wu, F., Mi, W., Cannon, S. C., *Neurology*, 2013, 80, 1110-1116 and Suetterlin, K. et at, *Current Opinion Neurology*, 2014, 27, 583-590) or hyperkalemic periodic paralysis which is an inherited autosomal dominant disorder that affects sodium channels in muscle cells and the ability to regulate potassium levels in the blood (Ammat, T. et at, *Journal of General Physiology*, 2015, 146, 509-525).

In a preferred embodiment the neuromuscular disorder is a myasthenic condition. Myasthenic conditions are characterized by muscle weakness and neuromuscular transmission failure. Congenital myasthenia gravis (Finlayson, S., Beeson, D., Palace, J. Congenital myasthenic syndromes: an update. *Pract. Neurol.*, 2013, 13, 80-91) is an inherited neuromuscular disorder caused by defects of several types at the neuromuscular junction.

Myasthenia gravis and Lambert-Eaton syndrome (Titulaer M J, Lang B, Verschuuren J J. Lambert-Eaton myasthenic syndrome: from clinical characteristics to therapeutic strategies. *Lancet Neurol.* 2011, 10, 1098-107) are examples of myasthenic conditions. Myasthenia gravis is either an autoimmune or congenital neuromuscular disorder that leads to fluctuating muscle weakness and fatigue. In the most common cases, muscle weakness is caused by circulating antibodies that block ACh receptors at the postsynaptic neuromuscular junction, inhibiting the excitatory effects of the neurotransmitter ACh on nicotinic ACh-receptors at neuromuscular junctions (Gilhus, N. E., Owe, J. F., Hoff, J. M., Romi, F., Skeie, G. O., Aarli, J. A. Myasthenia Gravis: A Review of Available Treatment Approaches, *Autoimmune Diseases*, 2011, Article ID 84739). Lambert-Eaton myasthenic syndrome (also known as LEMS, Lambert-Eaton syndrome, or Eaton-Lambert syndrome) is a rare autoimmune disorder that is characterized by muscle weakness of the limbs. It is the result of an autoimmune reaction in which antibodies are formed against presynaptic voltage-gated calcium channels, and likely other nerve terminal proteins, in the neuromuscular junction. Thus, in one embodiment of the present disclosure the neuromuscular disorder is myasthenia gravis. In another preferred embodiment the neuromuscular disorder is Lambert-Eaton syndrome.

Neuromuscular blockade is used in connection with surgery under general anaesthesia. Reversing agents are used for more rapid and safer recovery of muscle function after such blockade. Complications with excessive muscle weakness after blockade during surgery can result in delayed weaning from mechanical ventilation and respiratory complications after the surgery. Since such complications have pronounced effects on outcome of the surgery and future quality of life of patients, there is a need for improved reversing agents (Murphy G S, Brull S J. Residual neuromuscular block: lessons unlearned. Part I: definitions, incidence, and adverse physiologic effects of residual neuromuscular block. Anesth Analg. 2010 111(1):120-8). Thus, in one embodiment, the neuromuscular disorder has been induced by a neuromuscular blocking agent. In one particular embodiment the neuromuscular disorder is muscle weakness caused by neuromuscular blockade after surgery. In another preferred embodiment of the present disclosure the compound or the compound for use is used for reversing and/or ameliorating neuromuscular blockade after surgery. In one embodiment, the neuromuscular blockade is drug induced. In one embodiment the neuromuscular blockade is induced by an antibiotic. In one embodiment the neuromuscular blockade is induced by a non-depolarizing neuromuscular blocker.

Pharmaceutical Formulations

In one embodiment, a composition comprising the compound or the compound for use, according to the present disclosure, is provided. The composition according to the present disclosure is used for treating, ameliorating and/or preventing a neuromuscular disorder, and/or for use in reversing and/or ameliorating a neuromuscular blockade. Thus, it is preferred that the compositions and compounds described herein are pharmaceutically acceptable. In one embodiment the composition as described herein is in the form of a pharmaceutical formulation. In one embodiment, the composition as described herein further comprises a pharmaceutically acceptable carrier. Examples of potential formulations and preparations are contained, for example, in the Handbook of Pharmaceutical Excipients as well as Remington's Pharmaceutical Sciences.

Combination Therapy

The composition of the present disclosure may comprise further active ingredients/agents or other components to increase the efficiency of the composition.

Thus, in one embodiment the composition further comprises at least one further active agent. It is appreciated that the active agent is suitable for treating, preventing or ameliorating said neuromuscular disorder.

The active agent is in a preferred embodiment an acetylcholine esterase inhibitor. Said acetylcholine esterase inhibitor may for example be selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

Preferably the acetylcholine esterase inhibitor is selected from the group consisting of neostigmine, physostigmine and pyridostigmine. It is preferred that the acetylcholine esterase inhibitor is neostigmine or pyridostigmine.

The active agent may also be an immunosuppressive drug. Immunosuppressive drugs are drugs that suppress or reduce the strength of the body's immune system. They are also known as anti-rejection drugs. Immunosuppressive drugs include but are not limited to glucocorticoids, corticosteroids, cytostatics, antibodies and drugs acting on immunophilins. In one embodiment the active agent is prednisone.

The active agent may also be an agent that is used in anti-myotonic treatment. Such agents include for example blockers of voltage gated $Na^+$ channels, and aminoglycosides.

The active agent may also be an agent for reversing a neuromuscular blockade after surgery. Such agents include for example neostigmine or sugammadex (Org 25969, tradename Bridion). The active agent may also be an agent for increasing the $Ca^{2+}$ sensitivity of the contractile filaments in muscle. Such agents include tirasemtiv and CK-2127107 (Hwee, D. T., Kennedy, A. R., Hartman, J. J., Ryans, J., Durham, N., Malik, F. I., Jasper, J. R. The small-molecule fast skeletal troponin activator, CK-2127107, improves exercise tolerance in a rat model of heart failure. Journal of Pharmacology and Experimental Therapeutics, 2015, 353, 159-168).

The active agent may also be an agent for increasing ACh release by blocking voltage-gated $K^+$ channels in the presynaptic terminal. Such agent includes 3,4-aminopyridine.

Methods

In one aspect, the present disclosure relates to a method of treating, preventing and/or ameliorating a neuromuscular disorder, said method comprising administering a therapeutically effective amount of the compound or the compound for use as defined herein to a person in need thereof. In one embodiment, the person is a human being.

In one aspect, the present disclosure relates to a method of reversing and/or ameliorating a neuromuscular blockade, said method comprising administering a therapeutically effective amount of the compound or the compound for use as defined herein to a person in need thereof.

In one aspect, the present disclosure relates to a method for recovery of neuromuscular transmission, said method comprising administering a therapeutically effective amount of the compound or the compound for use as defined herein to a person in need thereof.

The person in need thereof may be a person having a neuromuscular disorder or a person at risk of developing a neuromuscular disorder or a person having symptoms of muscle weakness and/or fatigue. In another embodiment the person in need thereof is a person with reduced neuromuscular transmission safety with prolonged recovery after neuromuscular blockade. Types of neuromuscular disorders are defined herein above. In a preferred embodiment the person has, amyotrophic lateral sclerosis, spinal muscular atrophy, myasthenia gravis or Lambert-Eaton syndrome.

A therapeutically effective amount is an amount that produces a therapeutic response or desired effect in the person taking it. Administration routes, formulations and dosages can be determined by persons of skill in the art.

The method of treatment may be combined with other methods that are known to treat, prevent and/or ameliorate neuromuscular disorders. The treatment method may for example be combined with administration of any of the agents mentioned herein above. In one embodiment the treatment is combined with administration of acetylcholine esterase inhibitor such as for example neostigmine or pyridostigmine.

Another aspect of the disclosure relates to use of a compound as defined herein, for the manufacture of a medicament for the treatment, prevention and/or amelioration of a neuromuscular disorder.

Another aspect relates to use of a compound as defined herein, for the manufacture of a medicament or a reversal agent for reversing and/or ameliorating a neuromuscular blockade after surgery.

Method of Manufacturing

In one aspect, the present disclosure relates to methods of manufacturing compounds or compounds for use according to formula (I).

One method for manufacturing the compounds or compounds for use according to the present disclosure comprises the steps of
a. reacting a compound having formula (GM.II)

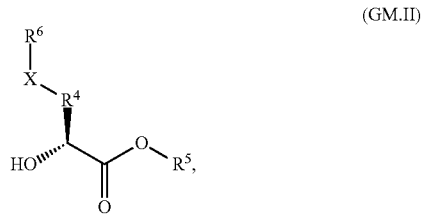

(GM.II)

wherein $R^4$, $R^5$, $R^6$ and X are defined herein with a compound having formula (GM.I) under Mitsunobu or similar reaction conditions

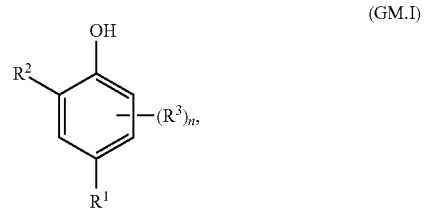

(GM.I)

wherein $R^1$, $R^2$, $R^3$ and n are as defined herein to generate a compound having formula (GM.III)

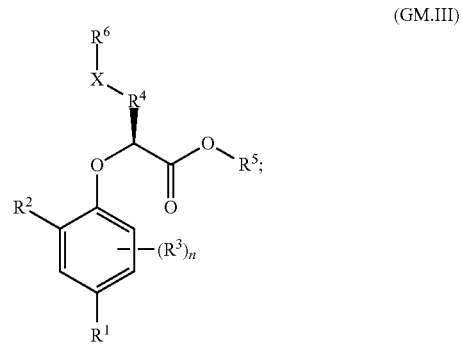

(GM.III)

and
b. reacting the product compound of a) with an ester hydrolysing reagent thus generating a compound as defined herein.

One method for manufacturing the compounds or compounds for use according to the present disclosure comprises the steps of
a. reacting a compound having formula (GM.V)

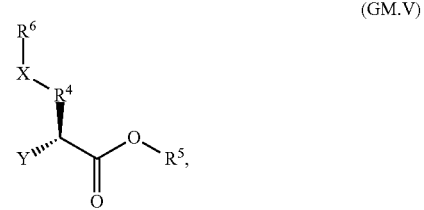

(GM.V)

wherein $R^4$, $R^5$, $R^6$ and X are defined herein and Y is a leaving group (for example a halogen, methanesulphonate or a tosylate) with a compound having formula (GM.I) under conditions which involve a suitable base such a sterically hindered amine or an alkali metal carbonate

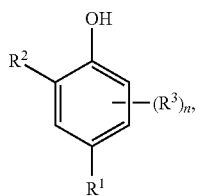

(GM.I)

wherein $R^1$, $R^2$, $R^3$ and n are as defined herein to generate a compound having formula (GM.III)

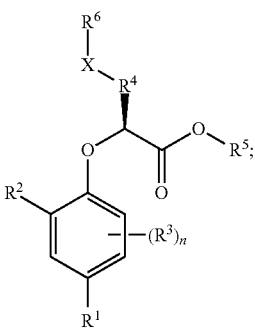

(GM.III)

and b. reacting the product compound of a) with an ester hydrolysing reagent thus generating a compound as defined herein.

One method for manufacturing the compounds or compounds for use according to the present disclosure comprises the steps of a. reacting a compound having formula (GM.II)

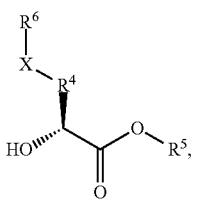

(GM.II)

wherein $R^4$, $R^5$, $R^6$ and X are defined herein with a compound having formula (GM.VI)

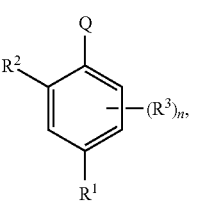

(GM.VI)

wherein $R^1$, $R^2$, $R^3$ and n are as defined herein and Q is a suitable leaving group such as fluorine or iodine, to generate a compound having formula (GM.III)

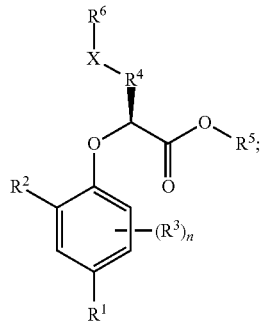

(GM.III)

and b. reacting the product compound of a) with an ester hydrolysing reagent thus generating a compound as defined herein.

One method for manufacturing the compounds or compounds for use according to the present disclosure comprises the steps of a. reacting a compound having formula (GM.VII)

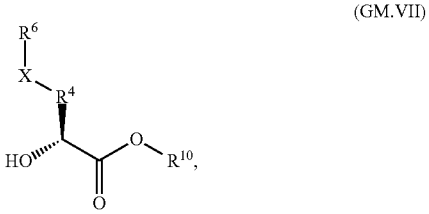

(GM.VII)

wherein $R^4$, $R^6$ and X are defined herein and $R_{10}$ is a suitable protecting group, such as a silyl-containing moiety, with a compound having formula (GM.I) under Mitsunobu or similar reaction conditions

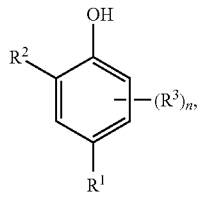

(GM.I)

wherein $R^1$, $R^2$, $R^3$ and n are as defined herein to generate a compound having formula (GM.VIII)

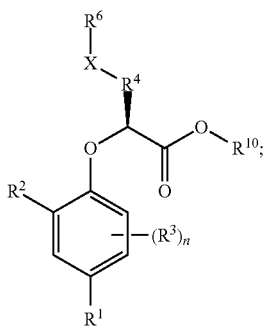

(GM.VIII)

b. removing the protecting group $R^{10}$ of product compound of a); and
c. reacting the product compound of b) with an oxidising reagent thus generating a compound as defined herein.

Items
1. A compound of Formula (I):

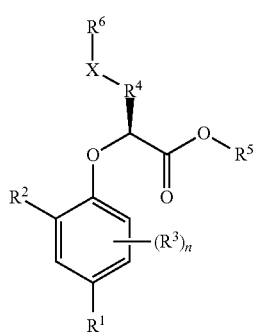

Formula (I)

wherein:
$R^1$ is selected from the group consisting of F, Cl, Br and I;
$R^2$ is selected from the group consisting of $C_{2-5}$ alkyl optionally substituted with one or more, identical or different, substituents $R^8$ and $C_{3-5}$ cycloalkyl optionally substituted with one or more, identical or different, substituents $R^8$ and wherein one —CH$_2$— in the $C_{2-5}$ alkyl or $C_{3-5}$ cycloalkyl is optionally replaced by —O—;
$R^3$ is selected from the group consisting of deuterium, Cl and F;
$R^4$ is $C_{1-3}$ alkanediyl which may be optionally substituted with one or more, identical or different, substituents $R^8$;
$R^5$ is selected from the group consisting of H, $C_{1-5}$ alkyl, $C_{2-5}$ alkenyl, $C_{2-5}$ alkynyl, and $C_{3-6}$ cycloalkyl, each of which may be optionally substituted with one or more, identical or different, substituents $R^7$; phenyl optionally substituted with one or more, identical or different, substituents $R^9$; and benzyl optionally substituted with one or more, identical or different, substituents $R^9$;
$R^6$ is selected from the group consisting of $C_{1-5}$ alkyl and $C_{3-5}$ cycloalkyl, each of which may be optionally substituted with one or more, identical or different, substituents $R^7$;
$R^7$ is independently selected from the group consisting of deuterium and F;
$R^8$ is independently selected from the group consisting of deuterium, F and $C_{1-3}$ alkyl optionally substituted with one or more, identical or different, substituents $R^7$;
$R^9$ is independently selected from the group consisting of deuterium, methoxy, nitro, cyano, Cl, Br, I and F; and
n is an integer 0, 1, 2 or 3; and
X is O, S, SO or SO$_2$;
or a pharmaceutically acceptable salt, hydrate, polymorph, tautomer, or solvate thereof.

2. The compound according to any one of the preceding items, wherein the compound is of Formula (I):

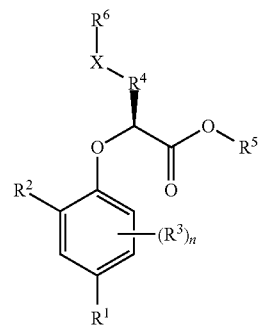

Formula (I)

wherein:
$R^1$ is selected from the group consisting of F, Cl, Br and I;
$R^2$ is selected from the group consisting of $C_{2-5}$ alkyl optionally substituted with one or more, identical or different, substituents $R^7$ and $C_{3-5}$ cycloalkyl optionally substituted with one or more, identical or different, substituents $R^7$ and wherein one —CH$_2$— is optionally replaced by —O— of said $C_{2-5}$ alkyl or $C_{3-5}$ cycloalkyl;
$R^3$ is selected from the group consisting of deuterium and F;
$R^4$ is $C_{1-3}$ alkanediyl which may be optionally substituted with one or more, identical or different, substituents $R^8$;
$R^5$ is selected from the group consisting of H, $C_{1-5}$ alkyl, $C_{2-5}$ alkenyl, $C_{2-5}$ alkynyl, $C_{3-6}$ cycloalkyl each of which may be optionally substituted with one or more, identical or different, substituents $R^7$, phenyl optionally substituted with one or more, identical or different, substituents $R^9$ and benzyl optionally substituted with one or more, identical or different, substituents $R^9$;
$R^6$ is selected from the group consisting of $C_{1-5}$ alkyl and $C_{3-5}$ cycloalkyl each of which may be optionally substituted with one or more, identical or different, substituents $R^7$;
$R^7$ is independently selected from the group consisting of deuterium and F;
$R^8$ is independently selected from the group consisting of deuterium, F and $C_{1-3}$ alkyl optionally substituted with one or more, identical or different, substituents $R^7$;

R$^9$ is independently selected from the group consisting of deuterium, methoxy, nitro, cyano, Cl, Br, I and F; and n is an integer 0, 1, 2 or 3; and X is O, S, SO or SO$_2$;

or a pharmaceutically acceptable salt, hydrate, polymorph, tautomer, or solvate thereof.

3. The compound according to any one of the preceding items, wherein the compound is of Formula (I):

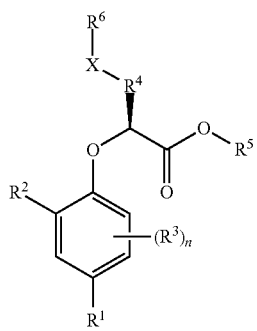

Formula (I)

wherein:
R$^1$ is selected from the group consisting of F, Cl, Br and I;

R$^2$ is selected from the group consisting of C$_{2-5}$ alkyl and C$_{3-5}$ cycloalkyl, each of which may be optionally substituted with one or more, identical or different, substituents R$^8$;

R$^3$ is selected from the group consisting of deuterium and F;

R$^4$ is C$_{1-3}$ alkanediyl which may be optionally substituted with one or more, identical or different, substituents R$^8$;

R$^5$ is selected from the group consisting of H, C$_{1-5}$ alkyl, C$_{2-5}$ alkenyl, C$_{2-5}$ alkynyl, and C$_{3-5}$ cycloalkyl, each of which may be optionally substituted with one or more, identical or different, substituents R$^7$; phenyl optionally substituted with one or more, identical or different, substituents R$^9$; and benzyl optionally substituted with one or more, identical or different, substituents R$^9$;

R$^6$ is selected from the group consisting of C$_{1-5}$ alkyl and C$_{3-5}$ cycloalkyl, each of which may be optionally substituted with one or more, identical or different, substituents R$^7$;

R$^7$ is independently selected from the group consisting of deuterium and F;

R$^8$ is independently selected from the group consisting of deuterium, F and C$_{1-3}$ alkyl optionally substituted with one or more, identical or different, substituents R$^7$;

R$^9$ is independently selected from the group consisting of deuterium, methoxy, nitro, cyano, Cl, Br, I and F; and n is an integer 0, 1, 2 or 3; and X is O or S;

or a pharmaceutically acceptable salt, hydrate, polymorph, tautomer, or solvate thereof.

4. The compound according to any one of the preceding items, wherein the compound is of Formula (II):

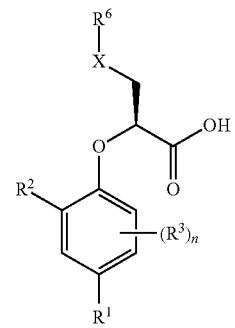

Formula (II)

wherein:
R$^1$ is selected from the group consisting of Cl and Br;

R$^2$ is C$_{3-5}$ cycloalkyl optionally substituted with one or more, identical or different, substituents R$^8$;

R$^3$ is selected from the group consisting of deuterium and F;

R$^6$ is selected from the group consisting of C$_{1-5}$ alkyl and C$_{3-5}$ cycloalkyl, each of which may be optionally substituted with one or more, identical or different, substituents R$^7$;

R$^7$ is independently selected from the group consisting of deuterium and F;

R$^8$ is independently selected from the group consisting of deuterium, F and C$_{1-3}$ alkyl optionally substituted with one or more, identical or different, substituents R$^7$;

n is an integer 0, 1, 2 or 3; and

X is O or S;

or a pharmaceutically acceptable salt, hydrate, polymorph, tautomer, or solvate thereof.

5. The compound according to any one of the preceding items, wherein the compound is of Formula (II):

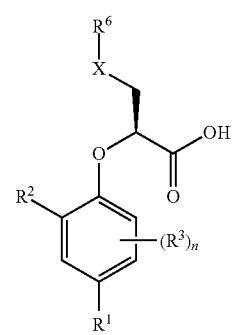

Formula (II)

wherein:
R$^1$ is selected from the group consisting of Cl and Br;

R$^2$ is selected from the group consisting of C$_{2-5}$ alkyl and C$_{3-5}$ cycloalkyl each of which may be optionally substituted with one or more, identical or different, substituents R$^7$;

R$^3$ is selected from the group consisting of deuterium and F;

R$^6$ is selected from the group consisting of C$_{1-5}$ alkyl and C$_{3-5}$ cycloalkyl each of which may be optionally substituted with one or more, identical or different, substituents R$^7$;

$R^7$ is independently selected from the group consisting of deuterium and F;

n is an integer 0, 1, 2 or 3; and

X is O or S;

or a pharmaceutically acceptable salt, hydrate, polymorph, tautomer, or solvate thereof.

6. The compound according to any one of the preceding items, wherein the compound is of Formula (III):

Formula (III)

[Chemical structure diagram showing a benzene ring with substituents including $R^6$, X, OH, O, cyclopropyl group with $(\_)_m$, $(R^3)_n$, and $R^1$]

wherein:
R¹ is selected from the group consisting of Cl and Br;
R³ is selected from the group consisting of deuterium and F;
R⁶ is selected from the group consisting of $C_{1-5}$ alkyl and $C_{3-5}$ cycloalkyl each of which may be optionally substituted with one or more, identical or different, substituents $R^7$;
$R^7$ is independently selected from the group consisting of deuterium and F;
m is an integer 1 or 2;
n is an integer 0, 1, 2 or 3; and
X is O or S;
or a pharmaceutically acceptable salt, hydrate, polymorph, tautomer, or solvate thereof.

7. The compound according to any one of the preceding items, wherein R¹ is Cl or Br.

8. The compound according to any one of the preceding items, wherein R¹ is Cl.

9. The compound according to any one of the preceding items, wherein R¹ is Br.

10. The compound according to any one of the preceding items, wherein R² is $C_{2-5}$ alkyl optionally substituted with one or more, identical or different, substituents $R^8$.

11. The compound according to any one of the preceding items, wherein R² is $C_{2-5}$ alkyl optionally substituted with one or more, identical or different, substituents $R^7$.

12. The compound according to any one of the preceding items, wherein R² is $C_{2-5}$ alkyl, preferably isopropyl.

13. The compound according to any one of the preceding items, wherein R² is $C_{2-5}$ alkyl substituted with one or more, identical or different, substituents $R^8$.

14. The compound according to any one of the preceding items, wherein R² is $C_{2-5}$ alkyl substituted with one or more, identical or different, substituents $R^7$.

15. The compound according to any one of the preceding items, wherein R² is isopropyl substituted with one or more, identical or different, substituents $R^8$.

16. The compound according to any one of the preceding items, wherein R² is isopropyl substituted with one or more, identical or different, substituents $R^7$.

17. The compound according to any one of the preceding items, wherein R² is $C_{3-5}$ cycloalkyl optionally substituted with one or more, identical or different, substituents $R^8$.

18. The compound according to any one of the preceding items, wherein R² is $C_{3-5}$ cycloalkyl optionally substituted with one or more, identical or different, substituents $R^7$.

19. The compound according to any one of the preceding items, wherein R² is $C_{3-5}$ cycloalkyl.

20. The compound according to any one of the preceding items, wherein R² is cyclopropyl or cyclobutyl, preferably cyclopropyl.

21. The compound according to any one of the preceding items, wherein R² is $C_{3-5}$ cycloalkyl substituted with one or more, identical or different, substituents $R^8$.

22. The compound according to any one of the preceding items, wherein R² is $C_{3-5}$ cycloalkyl substituted with one or more, identical or different, substituents $R^7$.

23. The compound according to any one of the preceding items, wherein R² is $C_{3-5}$ cycloalkyl substituted with one or more F.

24. The compound according to any one of the preceding items, wherein R² is $C_{3-5}$ cycloalkyl substituted with one or more deuterium.

25. The compound according to any one of the preceding items, wherein R² is cyclopropyl or cyclobutyl, preferably cyclopropyl, substituted with one or more deuterium and/or one or more F.

26. The compound according to any one of the preceding items, wherein R² is $C_{3-5}$ cycloalkyl wherein one —$CH_2$— is replaced by —O—.

27. The compound according to any one of the preceding items, wherein R² is oxiran-2-yl, oxetan-2-yl, oxetan-3-yl, oxolan-2-yl or oxolan-3-yl.

28. The compound according to any one of the preceding items, wherein R² is $C_{3-5}$ cycloalkyl substituted with $C_3$ alkyl optionally substituted with one or more, identical or different, substituents $R^7$.

29. The compound according to any one of the preceding items, wherein R² is selected from the group consisting of 1-methylcycloprop-1-yl, 1-ethylcycloprop-1-yl, 1-propylcycloprop-1-yl, (1-methylethyl)cycloprop-1-yl, 1-methylcyclobut-1-yl, 1-ethylcyclobut-1-yl, 1-propylcyclobut-1-yl, (1-methylethyl)cyclobut-1-yl, 1-methylcyclopent-1-yl, 1-ethylcyclopent-1-yl, 1-propylcyclopent-1-yl and (1-methylethyl)cyclopent-1-yl, each of which may be optionally substituted with one or more, identical or different, substituents $R^7$.

30. The compound according to any one of the preceding items, wherein R³ is deuterium.

31. The compound according to any one of the preceding items, wherein R³ is F.

32. The compound according to any one of the preceding items, wherein R³ is Cl.

33. The compound according to any one of the preceding items, wherein R³ is deuterium or F.

34. The compound according to any one of the preceding items, wherein R⁴ is $C_{1-3}$ alkanediyl, preferably methylene (—$CH_2$—).

35. The compound according to any one of the preceding items, wherein R⁴ is $C_{1-3}$ alkanediyl substituted with one or more, identical or different, substituents $R^8$.

36. The compound according to any one of the preceding items, wherein R⁴ is $C_{1-3}$ alkanediyl, such as methylene (—$CH_2$—), substituted with methyl.

37. The compound according to any one of the preceding items, wherein $R^5$ is H.
38. The compound according to any one of the preceding items, wherein $R^5$ is $C_{1-5}$ alkyl optionally substituted with one or more, identical or different, substituents $R^7$.
39. The compound according to any one of the preceding items, wherein $R^5$ is selected from the group consisting of methyl, ethyl, propyl, butyl and pentyl.
40. The compound according to any one of the preceding items, wherein $R^5$ is $C_{3-6}$ cycloalkyl optionally substituted with one or more, identical or different, substituents $R^7$.
41. The compound according to any one of the preceding items, wherein $R^5$ is selected from the group consisting of cyclopropyl, cyclobutyl, cyclopentyl and cyclohexyl.
42. The compound according to any one of the preceding items, wherein $R^5$ is phenyl optionally substituted with one or more, identical or different, substituents $R^9$.
43. The compound according to any one of the preceding items, wherein $R^5$ is benzyl optionally substituted with one or more, identical or different, substituents $R^9$.
44. The compound according to any one of the preceding items, wherein $R^6$ is $C_{3-5}$ alkyl optionally substituted with one or more, identical or different, substituents $R^7$.
45. The compound according to any one of the preceding items, wherein $R^6$ is $C_{3-5}$ cycloalkyl optionally substituted with one or more, identical or different, substituents $R^7$.
46. The compound according to any one of the preceding items, wherein $R^6$ is $C_{1-5}$ alkyl substituted with one or more, identical or different, substituents $R^7$.
47. The compound according to any one of the preceding items, wherein $C_{3-5}$ cycloalkyl substituted with one or more, identical or different, substituents $R^7$.
48. The compound according to any one of the preceding items, wherein $R^6$ is $C_{1-3}$ alkyl optionally substituted with one or more, identical or different, substituents $R^7$.
49. The compound according to any one of the preceding items, wherein $R^6$ is methyl optionally substituted with one or more, identical or different, substituents $R^7$.
50. The compound according to any one of the preceding items, wherein, $R^6$ is ethyl optionally substituted with one or more, identical or different, substituents $R^7$.
51. The compound according to any one of the preceding items, wherein $R^6$ is n-propyl optionally substituted with one or more, identical or different, substituents $R^7$.
52. The compound according to any one of the preceding items, wherein $R^6$ is isopropyl optionally substituted with one or more, identical or different, substituents $R^7$.
53. The compound according to any one of the preceding items, wherein $R^6$ is cyclopropyl optionally substituted with one or more, identical or different, substituents $R^7$.
54. The compound according to any one of the preceding items, wherein $R^6$ is cyclobutyl optionally substituted with one or more, identical or different, substituents $R^7$.
55. The compound according to any one of the preceding items, wherein $R^6$ is cyclopentyl optionally substituted with one or more, identical or different, substituents $R^7$.
56. The compound according to any one of the preceding items, wherein $R^7$ is deuterium.
57. The compound according to any one of the preceding items, wherein $R^7$ is F.
58. The compound according to any one of the preceding items, wherein $R^3$ is deuterium.
59. The compound according to any one of the preceding items, wherein $R^8$ is F.
60. The compound according to any one of the preceding items, wherein $R^8$ is $C_{1-3}$ alkyl optionally substituted with one or more, identical or different, substituents $R^7$.
61. The compound according to any one of the preceding items, wherein $R^3$ is methyl optionally substituted with one or more, identical or different, substituents $R^7$.
62. The compound according to any one of the preceding items, wherein $R^8$ is ethyl optionally substituted with one or more, identical or different, substituents $R^7$.
63. The compound according to any one of the preceding items, wherein $R^3$ is n-propyl optionally substituted with one or more, identical or different, substituents $R^7$.
64. The compound according to any one of the preceding items, wherein $R^3$ is isopropyl optionally substituted with one or more, identical or different, substituents $R^7$.
65. The compound according to any one of the preceding items, wherein m is 1.
66. The compound according to any one of the preceding items, wherein m is 2.
67. The compound according to any one of the preceding items, wherein n is 0.
68. The compound according to any one of the preceding items, wherein n is 1.
69. The compound according to any one of the preceding items, wherein n is 2.
70. The compound according to any one of the preceding items, wherein n is 3.
71. The compound according to any one of the preceding items, wherein X is O.
72. The compound according to any one of the preceding items, wherein X is S.
73. The compound according to any one of the preceding items, wherein X is O or S.
74. The compound according to any one of the preceding items, wherein X is SO.
75. The compound according to any one of the preceding items, wherein X is $SO_2$.
76. The compound according to any one of the preceding items, wherein, the compound is selected from the list consisting of:
  (2S)-2-(4-bromo-2-cyclopropylphenoxy)-3-methoxypropanoic acid;
  (2S)-2-(4-bromo-2-cyclopropylphenoxy)-3-ethoxypropanoic acid;
  (2S)-2-(4-bromo-2-cyclopropyl-5-fluorophenoxy)-3-methoxypropanoic acid;
  (2S)-2-[4-bromo-2-(1-ethylcyclopropyl)phenoxy]-3-methoxypropanoic acid;
  (2S)-2-(4-bromo-2-cyclopropylphenoxy)-3-(difluoromethoxy)propanoic acid;
  (2S)-2-(4-chloro-2-cyclopropylphenoxy)-3-methoxypropanoic acid;
  (2S)-2-(4-bromo-2-cyclopropylphenoxy)-3-methoxybutanoic acid;
  (2S,3S)-2-(4-chloro-2-cyclopropyl-5-fluorophenoxy)-3-methoxypropanoic acid;
  (2R)-2-(4-bromo-2-cyclobutylphenoxy)-3-(methylsulfanyl)propanoic acid;
  (2S)-2-(4-bromo-2-cyclobutylphenoxy)-3-methoxypropanoic acid;
  (2S)-2-(4-bromo-2-cyclopropylphenoxy)-4-methoxybutanoic acid;

(2R)-2-(4-bromo-2-cyclopropylphenoxy)-3-(methylsulfanyl)propanoic acid; and (2S)-2-[4-bromo-2-(propan-2-yl)phenoxy]-3-methoxypropanoic acid.

77. The compound according to any one of the preceding items, wherein the compound has activity on ClC-1 receptor.

78. The compound according to any one of the preceding items, wherein the compound is an inhibitor of the ClC-1 ion channel.

79. The compound according to item 80, wherein the $EC_{50}$<50 µM, preferably <40 µM, more preferably <30 µM, more preferably <20 µM, more preferably <15 µM, and most preferably <10 µM.

80. The compound according to any one of the preceding items, wherein the recovery of force in muscles with neuromuscular dysfunction is >5%, preferably >10%, more preferably >15%, more preferably >20%, more preferably >25%, even more preferably >30% and most preferably >35%.

81. The compound according to any one of the preceding items, wherein the compound improves the recovered force in isolated rat soleus muscles after exposure to tubocurarine.

82. A composition comprising the compound according to any one of the preceding items.

83. The composition according to any one of the preceding items, wherein the composition is a pharmaceutical composition.

84. The composition according to any one of the preceding items, wherein the composition further comprises a pharmaceutically acceptable carrier.

85. The composition according to any one of the preceding items, wherein the composition further comprises at least one further active agent.

86. The composition according to any one of the preceding items, wherein said further active agent is suitable for treating, preventing or ameliorating said neuromuscular disorder.

87. The composition according to any one of the preceding items, wherein said further active agent is an acetylcholine esterase inhibitor.

88. The composition according to any one of the preceding items, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine piperidines, donepezil, tacrine, edrophonium, huperzine, ladostigil, ungeremine and lactucopicrin.

89. The composition according to any one of the preceding items, wherein said acetylcholine esterase inhibitor is neostigmine or pyridostigmine.

90. The composition according to any one of the preceding items, wherein said further active agent is sugammadex.

91. The composition according to any one of the preceding items, wherein said further active agent is tirasemtiv or CK-2127107.

92. The composition according to any one of the preceding items, wherein said further active agent is 3,4-aminopyridine.

93. A method for manufacturing the compound according to any one of the preceding items, the method comprising the steps of
a. reacting a compound having formula (GM.II)

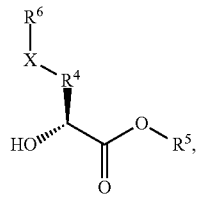

(GM.II)

wherein $R^4$, $R^5$, $R^6$ and X are as defined in any one of the preceding items with a compound having formula (GM.I)

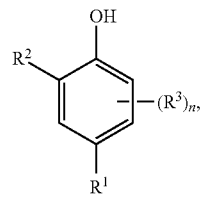

(GM.I)

wherein $R^1$, $R^2$, $R^3$ and n are as defined in any one of the preceding items to generate a compound having formula (GM.III)

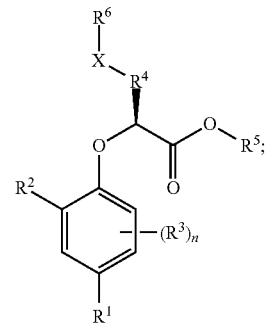

(GM.III)

b. reacting the product compound of a) with an ester hydrolysing reagent thus generating a compound according to any one of the preceding items.

94. A method for manufacturing the compound according to any one of the preceding items, the method comprising the steps of
a. reacting a compound having formula (GM.V)

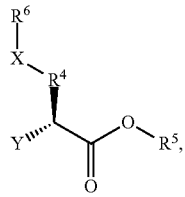

(GM.V)

wherein R⁴, R⁵, R⁶ and X are as defined in any one of the preceding items and Y is a leaving group with a compound having formula (GM.I)

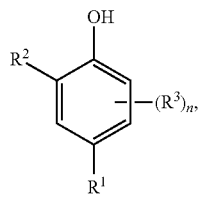
(GM.I)

wherein R¹, R², R³ and n are as defined in any one of the preceding items to generate a compound having formula (GM.III)

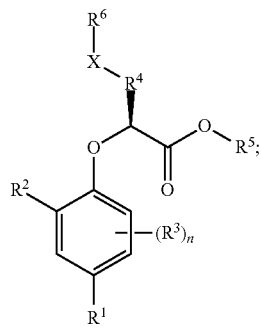
(GM.III)

and
  b. reacting the product compound of a) with an ester hydrolysing reagent thus generating a compound according to any one of the preceding items.

95. A method for manufacturing the compound according to any one of the preceding items, the method comprising the steps of
  a. reacting a compound having formula (GM.II)

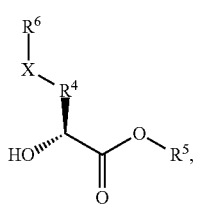
(GM.II)

wherein R⁴, R⁵, R⁶ and X are as defined in any one of the preceding items with a compound having formula (GM.VI)

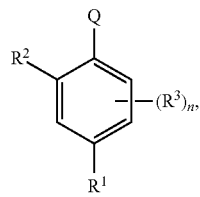
(GM.VI)

wherein R¹, R², R³ and n are as defined in any one of the preceding items and Q is a suitable leaving group, to generate a compound having formula (GM.III)

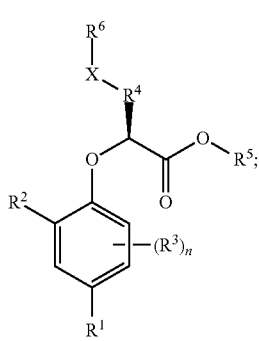
(GM.III)

and
  b. reacting the product compound of a) with an ester hydrolysing reagent thus generating a compound according to any one of the preceding items.

96. A method for manufacturing the compound according to any one of the preceding items, the method comprising the steps of
  a. reacting a compound having formula (GM.VII)

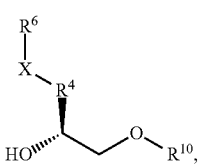
(GM.VII)

wherein R⁴, R⁶ and X are as defined in any one of the preceding items and R₁₀ is a suitable protecting group, with a compound having formula (GM.I)

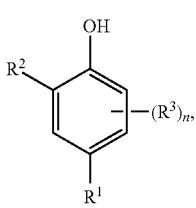
(GM.I)

wherein R¹, R², R³ and n are as defined in any one of the preceding items to generate a compound having formula (GM.VIII)

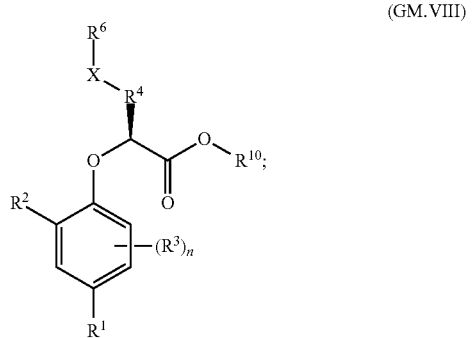

(GM.VIII)

b. removing the protecting group $R_{10}$ of product compound of a); and
c. reacting the product compound of b) with an oxidising reagent thus generating a compound according to any one of the preceding items.

97. The compound or the composition according to any one of the preceding items, for use as a medicament.
98. The compound according to any one of the preceding items for use in treating, ameliorating and/or preventing a neuromuscular disorder, and/or for use in reversing and/or ameliorating a neuromuscular blockade.
99. The compound for use according to any one of the preceding items wherein the neuromuscular disorder is myasthenia gravis.
100. The compound for use according to any one of the preceding items wherein the neuromuscular disorder is autoimmune myasthenia gravis.
101. The compound for use according to any one of the preceding items wherein the neuromuscular disorder is congenital myasthenia gravis.
102. The compound for use according to any one of the preceding items wherein the neuromuscular disorder is Lambert-Eaton Syndrome.
103. The compound for use according to any one of the preceding items wherein the neuromuscular disorder is critical illness myopathy.
104. The compound for use according to any one of the preceding items wherein the neuromuscular disorder is amyotrophic lateral sclerosis (ALS).
105. The compound for use according to any one of the preceding items wherein the neuromuscular disorder is spinal muscular atrophy (SMA).
106. The compound for use according to any one of the preceding items wherein the neuromuscular disorder is critical illness myopathy (CIM).
107. The compound for use according to any one of the preceding items wherein the neuromuscular disorder is Charcot-Marie tooth disease (CMT).
108. The compound for use according to any one of the preceding items wherein the neuromuscular disorder is sarcopenia.
109. The compound for use according to any one of the preceding items wherein the neuromuscular disorder arises from diabetic polyneuropathy.
110. The compound for use according to any one of the preceding items wherein the neuromuscular disorder is periodic paralysis.
111. The compound for use according to any one of the preceding items wherein the neuromuscular disorder is hypokalemic periodic paralysis or hyperkalemic periodic paralysis.
112. The compound for use according to any one of the preceding items wherein the neuromuscular disorder is selected from the group consisting of Guillain-Barre syndrome, poliomyelitis, post-polio syndrome, chronic fatigue syndrome, and critical illness polyneuropathy.
113. The compound for use according to any one of the preceding items, wherein the compound is for use in the treatment of symptoms of an indication selected from the group consisting of myasthenia gravis (such as autoimmune and congenital myasthenia gravis), Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barre syndrome, poliomyelitis, post-polio syndrome, chronic fatigue syndrome, critical illness polyneuropathy, periodic paralysis, sarcopenia, hypokalemic periodic paralysis and hyperkalemic periodic paralysis.
114. The compound for use according to any one of the preceding items wherein the neuromuscular disorder has been induced by a neuromuscular blocking agent.
115. The compound for use according to any one of the preceding items, wherein the neuromuscular blockade is neuromuscular blockade after surgery.
116. The compound for use according to any one of the preceding items wherein the neuromuscular blockade is drug induced.
117. The compound for use according to any one of the preceding items, wherein the drug is an antibiotic.
118. The compound for use according to any one of the preceding items, wherein the drug is a non-depolarizing neuromuscular blocker.
119. The compound for use according to any one of the preceding items, wherein said compound further has been modified in order to increase its half-life when administered to a patient, in particular its plasma half-life.
120. The compound for use according to any one of the preceding items, wherein said compound further comprises a moiety conjugated to said compound, thus generating a moiety-conjugated compound.
121. The compound for use according to any one of the preceding items, wherein the moiety-conjugated compound has a plasma and/or serum half-life being longer than the plasma and/or serum half-life of the non-moiety conjugated compound.
122. The compound for use according to any one of the preceding items, wherein the moiety conjugated to the compound is one or more type(s) of moieties selected from the group consisting of albumin, fatty acids, polyethylene glycol (PEG), acylation groups, antibodies and antibody fragments.
123. The compound for use according to any one of the preceding items, wherein said compound is comprised in a composition.
124. The compound for use according to any one of the preceding items, wherein the composition is a pharmaceutical composition.
125. The compound for use according to any one of the preceding items, wherein the composition further comprises a pharmaceutically acceptable carrier.
126. The compound for use according to any one of items, wherein the composition further comprises at least one further active agent.

127. The compound for use according to any one of the preceding items, wherein said further active agent is suitable for treating, preventing or ameliorating said neuromuscular disorder.

128. The compound for use according to any one of the preceding items, wherein said further active agent is an acetylcholine esterase inhibitor.

129. The compound for use according to any one of the preceding items, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

130. The compound for use according to any one of the preceding items, wherein said acetylcholine esterase inhibitor is neostigmine or pyridostigmine.

131. The compound for use according to any one of the preceding items, wherein said further active agent is sugammadex.

132. The compound for use according to any one of the preceding items, wherein said further active agent is tirasemtiv.

133. The compound for use according to any one of the preceding items, wherein said further active agent is 3,4-aminopyridine.

134. A method of treating, preventing and/or ameliorating a neuromuscular disorder, said method comprising administering a therapeutically effective amount of the compound as defined in any one of the preceding items to a person in need thereof.

135. Use of a compound as defined in any one of the preceding items, for the manufacture of a medicament for the treatment, prevention and/or amelioration of a neuromuscular disorder, and/or for reversing and/or ameliorating of a neuromuscular blockade.

136. A method of reversing and/or ameliorating a neuromuscular blockade, said method comprising administering a therapeutically effective amount of the compound as defined in any one of the preceding items to a person in need thereof.

137. A method for recovery of neuromuscular transmission, said method comprising administering a therapeutically effective amount of the compound as defined in any one of the preceding items to a person in need thereof.

138. A method for recovering neuromuscular transmission, the method comprising administering a compound as defined in any one of the preceding items to an individual in need thereof.

EXAMPLES

Materials and Methods

Chemicals

Compounds for testing were obtained from different suppliers including Enamine, Vitas, and CanAm Bioresearch. For synthesis of particular compounds please see below.

NMR Spectra $^1$H-NMR spectra were recorded either on a Bruker AM-300 spectrometer and were calibrated using residual nondeuterated solvent as internal reference. Spectra were processed using Spinworks version 4.0 (developed by Dr. Kirk Marat, Department of Chemistry, University of Manitoba), or on a Bruker 400 MHZ Ultrashield plus equipped with probe BBO 400 MHz S1 5 mm with Z gradient probe or a Bruker 500 MHz Avance III HD spectrometer, equipped with a Bruker 5 mm SmartProbe™, calibrated using residual non-deuterated solvent as internal reference and spectra processed using topspin version 3.2.7.

LCMS Method 1

Waters Acquity UPLC, X-Select; column: Waters X-Select UPLC C18, 1.7 µm, 2.1×30 mm. Solvent A: 0.1% formic acid in water; solvent B: 0.1% formic acid in MeCN. Gradient 5-95% Solvent B over 3 minutes; detector: diode array.

LCMS Method 2

Waters Acquity UPLC, X-Select; column: Waters X-Select UPLC C18, 1.7 µm, 2.1×30 mm. Solvent A: 0.1% formic acid in water; solvent B: 0.1% formic acid in MeCN. Gradient 5-95% Solvent B over 10 minutes; detector: diode array.

LCMS Method 3

Mass spectrometry analysis was performed using a WATERS ACQUITY QDa Mass Detector with a WATERS2695 HPLC and a WATERS micromass with a WATERS 2795 HPLC. Mass spectra was processed using WATERS Masslynx software.

HPLC Method 1

The product was analysed by Waters 2695 HPLC consisting of a Waters 996 photodiode array detector, Kromasil Eternity C18, 5 µm, 4.6×150 mm column. Flow rate: 1 mL/minute, run time 20 minutes. Solvent C: Acetonitrile; solvent D: 0.1% formic acid in water. Gradient 10-100% Solvent C vs D over 15 minutes with monitoring at 280 nm. Chromatograms were processed using WATERS Empower software.

Acidic 2-Minute Method

LCMS analysis was carried out with a Waters Acquity UPLC system consist of an Acquity I Class Sample Manager-FL, an Acquity I Class Binary Solvent Manager and an Acquity UPLC Column Manager. UV detection was afforded with an Acquity UPLC PDA detector (scanning from 210 nm to 400 nm) and mass detection was afforded with an Acquity QDa detector (mass scanning from 100-1250 Da; positive and negative modes simultaneously). A Waters Acquity UPLC BEH C18 column (2.1×50 mm 1.7 mm) was used to achieve separation of analytes.

Samples were prepared by dissolving (with or without sonication) into 1 mL of 50% v/v MeCN in water. These solutions were filtered with 0.45 mm syringe filter before submitting for analysis. All solvents (including formic acid) used were HPLC grade.

Conditions: 0.1% v/v Formic acid in water [Eluent A]; 0.1% v/v Formic acid in MeCN [Eluent B]; Flow rate 0.8 mL/min; injection volume 2 mL and 1.5 min equilibration time between samples.

Gradient:

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic 2-Minute Method

Samples were prepared by dissolving (with or without sonication) into 1 mL of 50% v/v MeCN in water. These solutions were filtered with 0.45 mm syringe filter before submitting for analysis. All solvents (and ammonium bicarbonate) used (including 35% ammonia solution) were HPLC grade.

Conditions: 10 mM Ammonium Bicarbonate+0.1% v/v 35% ammonia solution [Eluent A]; 0.1% v/v 35% ammonia solution in MeCN [Eluent B]; Flow rate 0.8 mL/min; injection volume 2 mL and 1.5 min equilibration time between samples.

Gradient:

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Acidic 4-Minute Method

Samples were prepared by dissolving (with or without sonication) into 1 mL of 50% v/v MeCN in water. These solutions were filtered with 0.45 mm syringe filter before submitting for analysis. All solvents (including formic acid) used were HPLC grade.

Conditions: 0.1% v/v formic acid in water [Eluent A]; 0.1% v/v formic acid in MeCN [Eluent B]; Flow rate 0.8 mL/min; injection volume 2 mL and 1.5 min equilibration time between samples.

Gradient:

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Chiral SCF Method 1

Compounds were analysed using a Waters ACQUITY ultra-performance convergence chromatography (UPC2) system equipped with a binary solvent delivery pump, an auto-sampler, a column oven (CM-30S), a back pressure regulator, and a diode array detector.

Column: Lux A1 (4.6 mm×250 mm, 5 m).

Conditions: 40° C., 4 mL/min, isocratic 85:15 $CO_2$:ethanol (0.1% v/v TFA), 125 BarG.

Chiral SCF Method 2

Compounds were analysed using a Waters ACQUITY ultra-performance convergence chromatography (UPC2) system equipped with a binary solvent delivery pump, an auto-sampler, a column oven (CM-30S), a back pressure regulator, and a diode array detector.

Column: Lux A2 (4.6 mm×250 mm, 5 m).

Conditions: 40° C., 4 mL/min, isocratic 70:30 $CO_2$:acetonitrile (0.1% v/v TFA), 125 BarG.

Chiral SCF Method 3

Compounds were analysed using a Waters ACQUITY ultra-performance convergence chromatography (UPC2) system equipped with a binary solvent delivery pump, an auto-sampler, a column oven (CM-30S), a back pressure regulator, and a diode array detector.

Column: Lux C2 (4.6 mm×250 mm, 5 m).

Conditions: 40° C., 4 mL/min, isocratic 70:30 $CO_2$:ethanol (0.2% v/v $NH_3$), 125 BarG.

Chiral HPLC Method 1

HPLC instrument equipped with Agilent 1200 binary pump, Agilent 1200 variable wavelength detector (UV-vis detector) and a Shodex 150×4.5 mm, 3 μm chiral column. Flow rate 0.5 mL/minute. Solvent A: 0.05% $CH_3COOH$ and 0.2 M NaCl in water. Solvent B: acetonitrile. Chiral HPLC analysis was performed in isocratic conditions (75% of solvent-A and 25% of solvent-B) at 280 nm wavelength. Chromatograms were processed using Agilent ChemStation software.

General Synthetic Strategies

Compounds of formula (I) may be synthesized by the following general methods:

General Method A

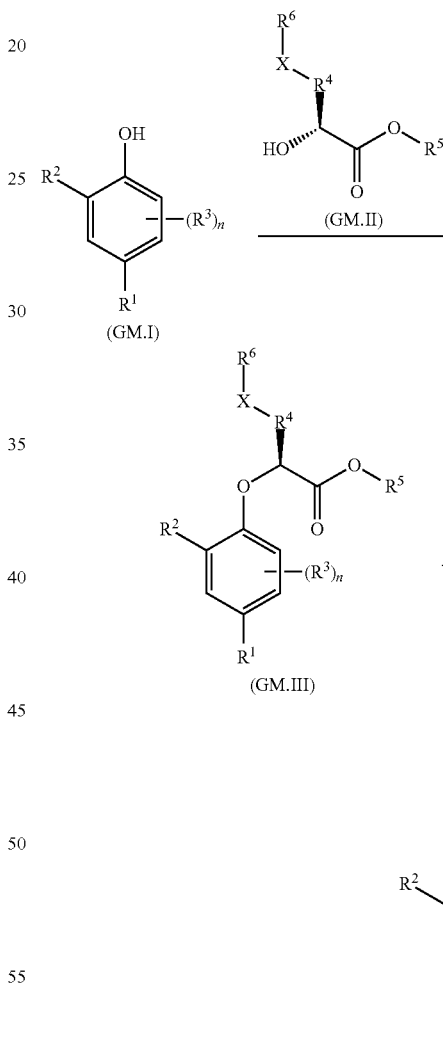

Method A involves the synthesis of compound GM.IV, which is an aryloxy α-substituted acetic acid derivative, and —$R^1$, —$R^2$, —$R^3$, —$R^4$, —$R^5$ and —$R^6$ are as defined in Formula (I) above. Phenols (GM.I) and hydroxyesters (GM.II) are available either commercially or synthetically and can be converted into an ether such as compound (GM.III) wherein $R^5$ is an alkyl or substituted alkyl group by methods which include variations on Mitsunobu reaction conditions. This ether (GM.III) contains an ester functionality —CO$_2$R$^5$, which can be hydrolysed under a range of standard conditions, involving acid or base, to provide the carboxylic acid of general structure (GM.IV). These standard conditions can also for example involve an enzyme-mediated hydrolysis, employing e.g. an esterase or lipase. If an ester molecule represented by (GM.III) includes for e.g. (CH$_3$)$_3$SiCH$_2$CH$_2$O— group as —O—R$^5$, then a fluoride ion source such as tetra-n-butyl-ammonium fluoride can be utilised to convert (GM.III) into the corresponding carboxylic acid (GM.IV).

Substituted phenols of general formula (GM.I) can be prepared by a variety of standard methods, for example by an ester rearrangement in the Fries rearrangement, by a rearrangement of N-phenylhydroxylamines in the Bamberger rearrangement, by hydrolysis of phenolic esters or ethers, by reduction of quinones, by replacement of an aromatic amine or by a hydroxyl group with water and sodium bisulfide in the Bucherer reaction. Other methods include the hydrolysis of diazonium salts, by rearrangement reaction of dienones in the dienone phenol rearrangement, by the oxidation of aryl silanes, by the Hock process.

Hydroxyesters of formula (GM.II) can be prepared e.g. by epoxide ring opening using a variety of alcohols or thiols under conditions such as those described in WO2010/015849.

General Method B

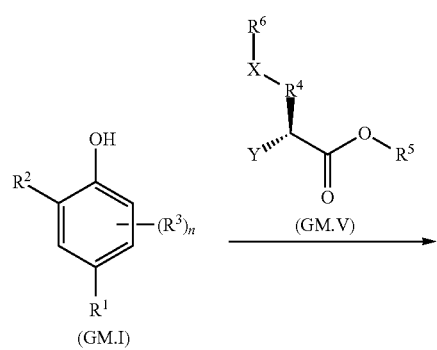

(GM.I) (GM.V)

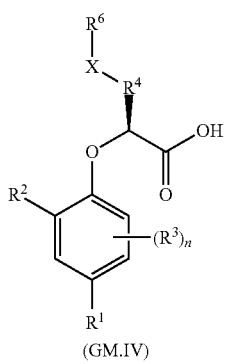

(GM.IV)

Method B involves the synthesis of compound (GM.IV), an aryloxy substituted acetic acid derivative, wherein —R$^1$, —R$^2$, —R$^3$, —R$^4$, —R$^1$ and —R$^6$ are as defined in Formula (I) above, and is related to Method A. The phenolic compound (GM.I) is available either commercially or synthetically, and can be converted into an ether such as (GM.III), wherein R$^5$ is an alkyl or a substituted alkyl group, by displacement of an appropriate leaving group Y, for example a halogen, methanesulphonate or a tosylate, under conditions which involve a suitable base such a sterically hindered amine or an alkali metal carbonate. The carboxylic acid (GM.IV) can be prepared by hydrolysis of compound (GM.III) by procedures described in Method A.

General Method C

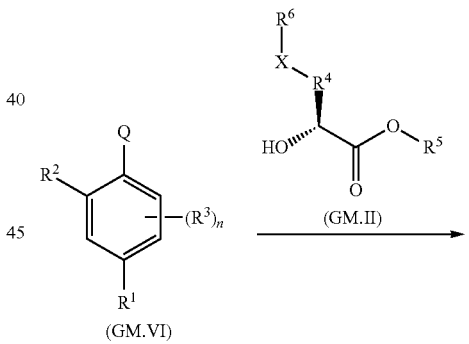

(GM.VI) (GM.II)

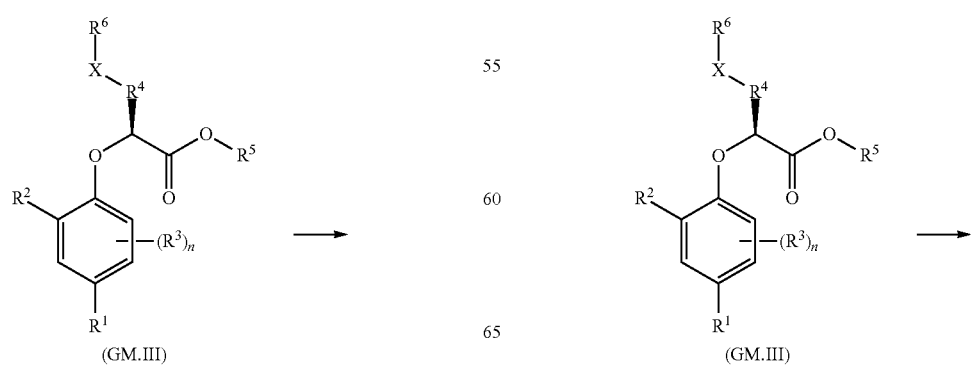

(GM.III) (GM.III)

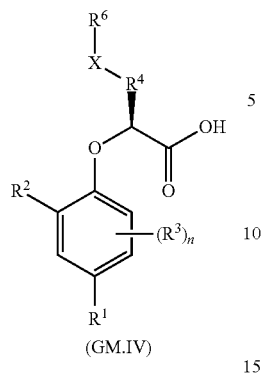

(GM.IV)

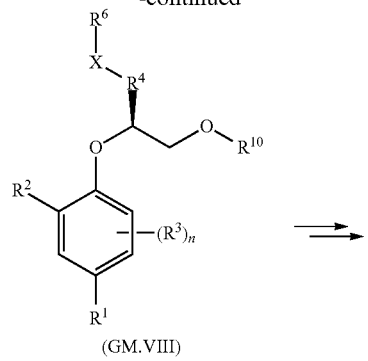

(GM.VIII)

Carboxylic acids of general formula (GM.IV), wherein —R$^1$, —R$^2$, —R$^3$, —R$^4$, —R$^5$ and —R$^6$ are as defined in Formula (I) above, can additionally be prepared by the procedure illustrated in General Method C. A phenolic ether of formula (GM.III), wherein R$^6$ can be an alkyl or substituted alkyl group, is prepared by displacement of a suitable leaving group Q in compound (GM.VI) by compound (GM.II). Q can for example be a halogen such as fluorine or iodine, and the ether product of formula I is be converted into the carboxylic acid derivative (GM.IV) by one of a range of standard methods outlined in Method A, involving hydrolysis of an ester functionality.

General Method D

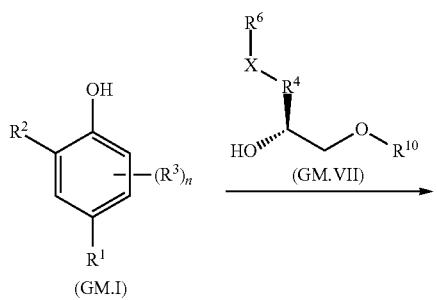

(GM.I)    (GM.VII)

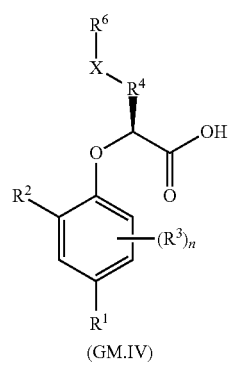

(GM.IV)

Carboxylic acids of general formula (GM.IV) can additionally be prepared by the procedure illustrated as General Method D), wherein —R$^1$, —R$^2$, —R$^3$, —R$^4$, —R and —R$^6$ are as defined in Formula (I) above. A phenolic ether of formula (GM.VIII) can be prepared by utilising e.g. appropriate Mitsunobu conditions involving the phenol structure (GM.I) and compound (GM.VII), wherein —R$^{10}$ is a suitable protecting group, such as a silyl-containing moiety. On removal of the protecting group —R$^{10}$, the primary alcohol (GM.VIII wherein R$^{10}$=H) can be oxidised to carboxylic acid (GM.IV) under standard conditions involving e.g. potassium permanganate, Jones oxidation conditions, the Heyns oxidation, ruthenium tetroxide or TEMPO.

Exemplified Compounds

Table 1 below illustrates Example compounds defined by the general Formula (I) which were prepared in >95% purity.

TABLE 1

Illustrative Examples of the Disclosure

| Cpd Number | IUPAC name | Spectroscopic data | Synthesis method |
|---|---|---|---|
| A-1 | (2S)-2-(4-Bromo-2-cyclopropylphenoxy)-3-methoxypropanoic acid | $^1$H NMR (400 MHz, DMSO-d$^6$) δ 7.12 (dd, J = 8.7, 2.6 Hz, 1H); 6.82 (d, J = 2.6 Hz, 1H); 6.64 (d, J = 8.8 Hz, 1H); 4.26 (dd, J = 8.2, 2.4 Hz, 1H); 3.77-3.55 (m, 2H); 3.29 (s, 3H); 2.22 (tt, J = 8.5, 5.3 Hz, 1H); 0.98-0.82 (m, 2H); 0.76-0.58 (m, 2H). LCMS method 2: m/z 313.4/315.5 (M-H)$^-$ (ES$^-$), at 4.307 min Chiral SCF method 1: (S)-enantiomer at 1.90 mins, >98% e.e. | A |

TABLE 1-continued

Illustrative Examples of the Disclosure

| Cpd Number | IUPAC name | Spectroscopic data | Synthesis method |
|---|---|---|---|
| A-2 | (2S)-2-(4-bromo-2-cyclopropyl-5-fluorophenoxy)-3-methoxypropanoic acid | $^1$H NMR (300 MHz, CDCl$_3$) δ 8.44-7.42 (br. s, 1H), 7.01 (d, 1H), 6.62 (d, 1H), 4.86-4.71 (br. s, 1H), 4.05-3.83 (m, 2H), 3.47 (s, 3H), 2.20-2.03 (m, 1H), 1.00-0.83 (m, 2H), 0.71-0.53 (m, 2H) $^{19}$F NMR (300 MHz, CDCl$_3$) δ -108.52 ppm MS (ES−): m/z 331.3 (M-H) HPLC method 1 retention time: 11.42 min. Chiral SCF method 3: (S)-enantiomer at 3.44 mins, >98% e.e. | B |
| A-3 | (2S)-2-(4-bromo-2-cyclopropylphenoxy)-3-(difluoromethoxy)propanoic acid | $^1$H NMR (300 MHz, CDCl$_3$) δ 8.97-7.99 (br. s, 1H), 7.20 (dd, 1H), 6.97 (d, 1H), 6.67 (d, 1H), 6.56-6.07 (t, 1H), 4.89 (t, 1H), 4.37 (d, 2H), 2.23-2.15 (m, 1H), 0.99-0.93 (m, 2H), 0.73-0.61 (m, 2H) $^{19}$F NMR (300 MHz, CDCl$_3$) δ -85.39 ppm MS (ES−): m/z 349.4 (M-H) HPLC method 1 retention time: 11.55 min Chiral HPLC method 1 retention time: 9.37 mins (97.9% e.e.) | D |
| A-4 | (2S)-2-(4-bromo-2-cyclopropylphenoxy)-3-methoxybutanoic acid | $^1$H NMR (300 MHz, CDCl$_3$) δ 7.17 (dd, 1H), 6.95 (d, 1H), 6.59 (d, 1H), 4.64 (d, 1H), 4.02-3.91 (m, 1H), 3.46 (s, 3H), 2.27-2.14 (m, 1H), 1.37 (d, 3H), 0.99-0.92 (m, 2H), 0.75-0.55 (m, 2H) MS (ES−): m/z 327.3 (M-H) HPLC method 1 retention time: 11.80 min. Chiral HPLC method 1 retention time: 9.28 mins. | A |
| A-5 | (2S, 3S)-2-(4-chloro-2-cyclopropyl-5-fluorophenoxy)-3-methoxypropanoic acid | See Example 4 | B |
| A-6 | (2S)-2-(4-bromo-2-cyclobutylphenoxy)-3-methoxypropanoic acid | See Example 5 | A |
| A-7 | (2S)-2-(4-bromo-2-cyclopropylphenoxy)-4-methoxybutanoic acid | $^1$H NMR (300 MHz, CDCl$_3$) δ 11.42-11.00 (br. s, 1H), 7.47 (dd, 1H), 7.25 (d, 1H), 6.92 (d, 1H), 5.13 (dd, 1H), 4.00-3.88 (m, 2H), 3.62 (s, 3H), 2.67-2.42 (m, 3H), 1.32-1.17 (m, 2H), 1.08-0.83 (m, 2H) MS (ES−): m/z 327.3 (M-H) HPLC method 1 retention time: 11.59 min. Chiral HPLC method 1 retention time: 8.66 mins (>98% e.e.) | A |

Example 1: Synthesis of 2-(4-bromo-2-cyclopropylphenoxy)-3-methoxypropanoic acid

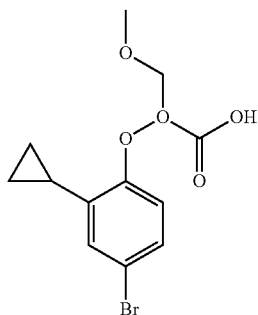

To a stirred solution of (R)-ethyl 2-hydroxy-3-methoxypropanoate (Foo, S. Y., U.S. Pat. Appl. Publ. (2012), US 20120122844 A1 2012.05.17; Iwaki, Y.; Kawanami, T.; Ksander, G. M.; Mogi, M. PCT Int. Appl. (2011), WO 2011061271 A1 2011.05.26) (200 mg, 1.350 mmol), 4-bromo-2-cyclopropylphenol (250 mg, 1.173 mmol) and triphenylphosphine (492 mg, 1.877 mmol) in THF (2 mL) at room temperature was added (E)-diisopropyl diazene-1,2-dicarboxylate (0.32 mL, 1.646 mmol) dropwise over 5 min. After 16 h. methanol (1 mL) was added and the solution evaporated in vacuo. The residue was subjected to column chromatography on silica gel (12 g cartridge, 0-50% EtOAc/isohexane) to afford a crude oil, which was dissolved in THF (2 mL) and MeOH (1 mL), and 2M sodium hydroxide solution (2 mL, 4.00 mmol) was added dropwise. After 16 h. the mixture was poured into water and the aqueous layer washed with EtOAc. The aqueous extracts were acidified with aq. HCl (1 M) and extracted with EtOAc. The organic extracts were dried over $MgSO_4$ and evaporated in vacuo. The residue was purified by column chromatography on silica gel (12 g cartridge, 0-50% EtOAc/isohexane) to afford 2-(4-bromo-2-cyclopropylphenoxy)-3-methoxypropanoic acid (70 mg, 0.211 mmol, 18% yield) as a white solid.

$^1$H NMR (400 MHz, DMSO-d$^6$) δ 13.16 (s, 1H); 7.23 (dd, J=8.7, 2.5 Hz, 1H); 6.94 (dd, J=2.5 Hz, 1H); 6.76 (d, J=8.8 Hz, 1H); 4.96 (dd, J=5.4, 2.9 Hz, 1H); 3.87 (dd, J=11.1, 5.3 Hz, 1H); 3.78 (dd, J=11.1, 2.9 Hz, 1H); 3.35 (s, 3H—obscured by H$_2$O peak); 2.19 (tt, J=8.5, 5.3 Hz, 1H); 0.92 (dq, J=8.5, 1.8 Hz, 2H); 0.81-0.59 (m, 2H).

LCMS method 1: m/z 313.4/315.6 (M-H)$^-$ (ES−), at 1.802 min.

Sodium 2-(4-bromo-2-cyclopropylphenoxy)-3-methoxypropanoate

To a solution of 2-(4-bromo-2-cyclopropylphenoxy)-3-methoxypropanoic acid (70 mg, 0.222 mmol) in methanol (2 mL) at 0° C. was added 1M sodium hydroxide volumetric solution (0.222 ml, 0.222 mmol). The solution was evaporated in vacuo and the residue co-evaporated with ethanol (5 mL) to provide a solid that was dried under vacuum at 45° C. overnight to afford sodium 2-(4-bromo-2-cyclopropylphenoxy)-3-methoxypropanoate (70 mg, 0.197 mmol, 89% yield) as a white solid.

1H NMR (400 MHz, DMSO-d$^6$) δ 7.12 (dd, J=8.7, 2.5 Hz, 1H); 6.82 (dd, J=2.6 Hz, 1H); 6.63 (d, J=8.8 Hz, 1H); 4.29 (dd, J=8.1, 2.4 Hz, 1H); 3.80-3.59 (m, 2H); 3.29 (s, 3H); 2.22 (tt, J=8.5, 5.3 Hz, 1H); 0.89 (dt, J=8.6, 2.1 Hz, 2H); 0.80-0.54 (m, 2H).

LCMS method 2: m/z 313.4/315.4 (M-H)$^-$ (ES−), at 2.345 min.

Example 2: Synthesis of (2S)- and (2R)-2-(4-bromo-2-cyclopropylphenoxy)-3-methoxypropanoic acid 2-(4-Bromo-2-cyclopropylphenoxy)-3-methoxypropanoic acid (470 mg) was dissolved to 50 mg/mL in isopropanol/dichloromethane (1:1 ratio) and was then purified by Supercritical Fluid Chromatography (SFC) on a Sepiatec Prep SFC 100 model under the following conditions.

Column: Lux A1 (30 mm×250 mm, 5 m).

Conditions: 40° C., 50 mL/min, isocratic 80:20 $CO_2$: isopropanol (0.1% v/v TFA), 100 BarG. Sequential injections of 250 μL (12.5 mg).

Combined fractions of the first eluting enantiomer were evaporated to near dryness using a rotary evaporator, transferred into final vessels with dichloromethane, which was removed on a Biotage V10 at 35° C. before being stored in a vacuum oven at ambient temperature and 5 mbar until constant weight to afford (S)-2-(4-bromo-2-cyclopropylphenoxy)-3-methoxypropanoic acid (200.4 mg), as an off-white solid.

Water (6 mL) was added to (S)-2-(4-bromo-2-cyclopropylphenoxy)-3-methoxypropanoic acid (200.4 mg, 0.636 mmol), the suspension cooled at 0° C. and 1 M sodium hydroxide volumetric solution (636 μl, 0.636 mmol) was added. The mixture was sonicated until all solid had dissolved. The solution was frozen and water removed by lyophilisation to afford sodium (S)-2-(4-bromo-2-cyclopropylphenoxy)-3-methoxypropanoate (190 mg, 0.536 mmol) as a white solid.

$^1$H NMR (400 MHz, DMSO-ds) δ 7.12 (dd, J=8.7, 2.6 Hz, 1H); 6.82 (d, J=2.6 Hz, 1H); 6.64 (d, J=8.8 Hz, 1H); 4.26 (dd, J=8.2, 2.4 Hz, 1H); 3.77-3.55 (m, 2H); 3.29 (s, 3H); 2.22 (tt, J=8.5, 5.3 Hz, 1H); 0.98-0.82 (m, 2H); 0.76-0.58 (m, 2H).

Chiral SCF method 1: (S)-enantiomer at 1.90 mins, 98.0% e.e.

Fractions containing the second eluting enantiomer were combined, concentrated, repurified and isolated as above to afford (R)-2-(4-bromo-2-cyclopropylphenoxy)-3-methoxypropanoic acid, which was converted into the corresponding sodium salt as described above.

Chiral SCF method 1: (R)-enantiomer at 3.36 mins, 94.8% e.e.

Example 3: Synthesis of 2-(4-bromo-2-cyclopropylphenoxy)-3-ethoxypropanoic acid

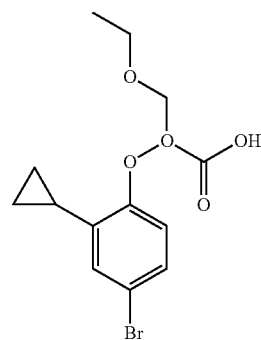

To a stirred solution of (R)-ethyl 3-ethoxy-2-hydroxypropanoate (Bock, M. G.; Watt, A. P.; Porter, R. A.; Harrison, D. PCT Int. Appl. (2019), WO 2019025467 A1 2019.02.07) (209 mg, 1.291 mmol), 4-bromo-2-cyclopropylphenol (250 mg, 1.173 mmol) and triphenylphosphine (492 mg, 1.877 mmol) in THF (10 mL) at room temperature was added (E)-diisopropyl diazene-1,2-dicarboxylate (0.32 mL, 1.646 mmol) dropwise. After 3 days stirring at ambient temperature MeOH (1 mL) was added and the solution evaporated in vacuo. The resultant residue was purified by chromatography on silica gel (12 g cartridge, 0-20% EtOAc/isohexane). The resulting partially purified product was dissolved in THF (5 mL); MeOH (1 mL) and 2M sodium hydroxide solution (1 mL, 2.0 mmol) were introduced dropwise. The resultant solution was stirred for 1 h, diluted with water and washed with EtOAc. The aqueous phase was acidified to pH ~2 and extracted with EtOAc. Organic extracts were dried over MgSO₄ and evaporated in vacuo. The residue was purified by chromatography on silica gel (4 g cartridge, 0-50% EtOAc/pentane) to afford 2-(4-bromo-2-cyclopropylphenoxy)-3-ethoxypropanoic acid (21.2 mg, 0.064 mmol, 5.5% yield) as a white solid.

LCMS method 1: m/z 327.5/329.5 (M-H)⁻ (ES-), at 1.907 min.

Sodium 2-(4-bromo-2-cyclopropylphenoxy)-3-ethoxypropanoate

To a solution of 2-(4-bromo-2-cyclopropylphenoxy)-3-ethoxypropanoic acid (21.2 mg, 0.064 mmol) in MeOH (0.5 mL) at 0° C. was added 1M sodium hydroxide volumetric solution (0.064 ml, 0.064 mmol). The solution was evaporated in vacuo and the residue co-evaporated with ethanol (5 ml) to give a solid that was dried under vacuum at 45° C. overnight to afford sodium 2-(4-bromo-2-cyclopropylphenoxy)-3-ethoxypropanoate (20.9 mg, 0.057 mmol, 88% yield) as a white solid.

¹H NMR (400 MHz, DMSO-d⁶) δ 7.12 (dd, J=8.8, 2.5 Hz, 1H); 6.82 (d, J=2.6 Hz, 1H); 6.63 (d, J=8.8 Hz, 1H); 4.23 (dd, J=8.5, 2.2 Hz, 1H); 3.76 (dd, J=11.0, 2.2 Hz, 1H); 3.64 (dd, J=11.1, 8.4 Hz, 1H); 3.48 (q, J=7.0 Hz, 2H); 2.21 (tt, J=8.5, 5.2 Hz, 1H); 1.09 (q, J=7.0 Hz, 3H); 0.97-0.81 (m, 2H); 0.80-0.59 (m, 2H).

LCMS method 2: m/z 327.2/329.3 (M-H)⁻ (ES-), at 2.634 min.

Example 4: Synthesis of (2S,3S)-2-(4-chloro-2-cyclopropyl-5-fluorophenoxy)-3-methoxypropanoic acid Compound A-5 was prepared following the synthetic route described below.

¹H NMR (300 MHz, CDCl₃) δ 9.70-8.70 (br. s, 1H); 6.87 (d, 1H); 6.64 (d, 1H); 4.80 (t, 1H); 4.02-3.87 (m, 2H); 3.49 (s, 3H); 2.21-2.05 (m, 1H); 1.03-0.85 (m, 2H); 0.72-0.54 (m, 2H)

¹⁹F NMR (300 MHz, CDCl₃) δ 116.35

MS (ES-): m/z 287 [M-1].

Chiral HPLC method 1 retention time: 11.26 min (91.5%). (2S,3R)-isomer at 10.48 mins (8.5%)

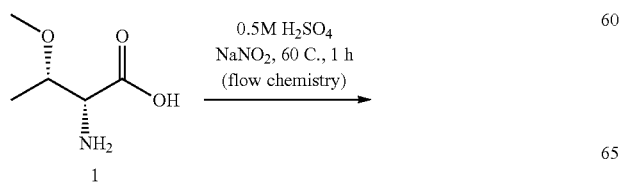

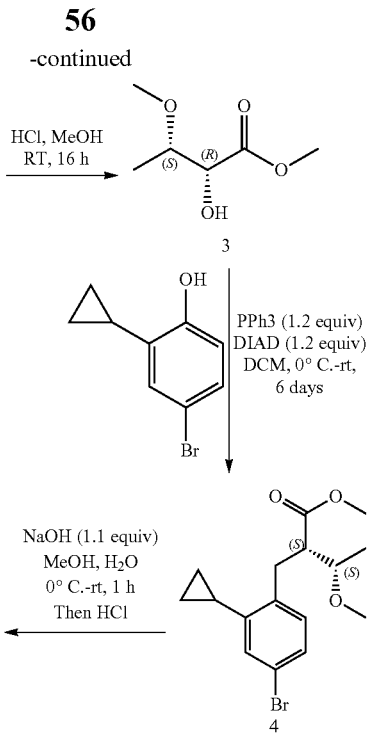

Example 5: Synthesis of sodium (S)-2-(4-bromo-2-cyclobutylphenoxy)-3-methoxypropanoate

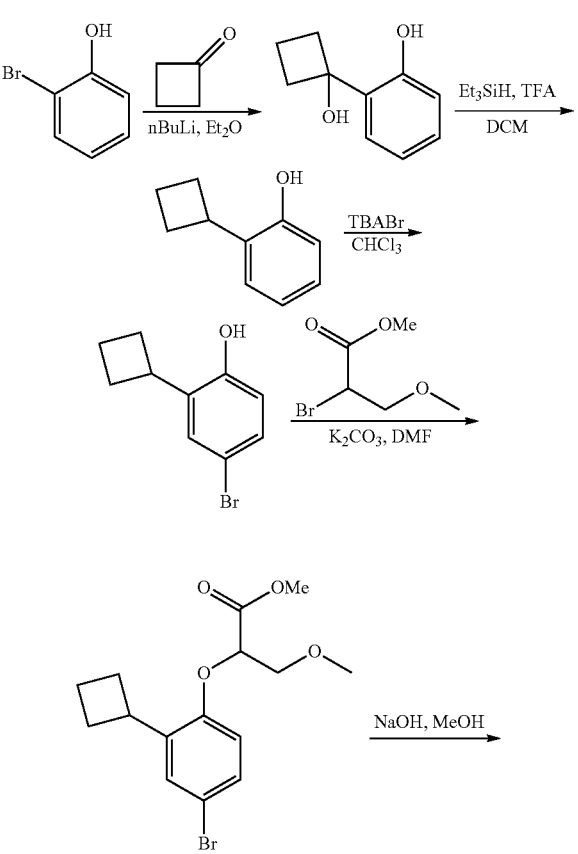

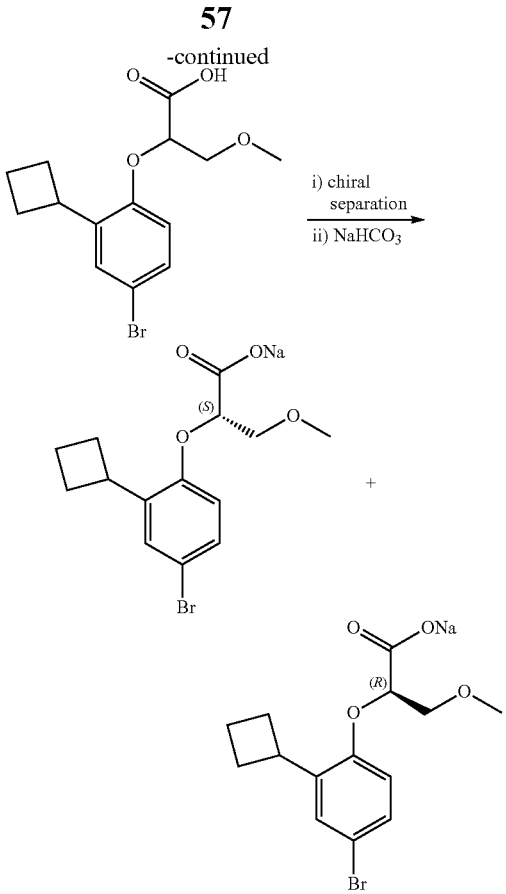

Step 1: Synthesis of 2-(1-hydroxycyclobutyl)phenol

To a cooled (−78° C.) mixture of 2-bromophenol (20.1 mL, 0.17 mol, 1.0 eq.) in diethyl ether (480 mL) was added dropwise n-butyl lithium (2.5 M in hexanes, 152.6 mL, 0.38 mol, 2.2 eq.). The mixture was stirred at that temperature for 10 min and then warmed to room temperature and stirred for 5 h. The mixture was re-cooled to −78° C., cyclobutanone (19.4 mL, 0.26 mol, 1.5 eq,) was added and the mixture was allowed to warm slowly to room temperature and stirred overnight. The reaction was quenched by the addition of saturated aqueous ammonium chloride solution (200 mL) and extracted with EtOAc (3×200 mL). The combined organic phases were washed with brine (500 mL), dried over sodium sulfate and concentrated under reduced pressure to give the title compound (34.5 g, 0.17 mol, 99%) as an oil orange residue which was used in the subsequent step without further purification.

UPLC-MS: acidic 2-minute run MS (ES−): no m/z; retention time: 0.93 min; purity: 68%. $^1$H NMR (400 MHz, Chloroform-d) δ 1.65 (dq, J=11.2, 8.4 Hz, 1H), 1.84-1.99 (m, 1H), 2.25-2.39 (m, 2H), 2.45-2.57 (m, 2H), 2.71 (s, 1H), 6.78-6.89 (m, 2H), 7.08-7.21 (m, 2H), 7.77 (s, 1H).

Step 2: Synthesis of 2-cyclobutylphenol

To a cooled (0° C.) solution of 2-(1-hydroxycyclobutyl) phenol (34.5 g, 0.21 mol, 1.0 eq.) in DCM (376 mL) was added triethylsilane (252.1 mL, 0.63 mol, 3.0 eq.) and the reaction stirred at 0° C. for 30 min prior to the addition of trifluoroacetic acid (62.7 mL, 0.82 mol, 3.9 eq.). The reaction mixture was allowed to slowly warm to room temperature and stirred overnight. The reaction was concentrated under reduced pressure and the resultant product was dried under vacuum for 2 h to give the title compound (40.0 g, 0.21 mol, 99%) as an orange oil which was used in the subsequent step without further purification.

UPLC-MS: acidic 2-minute run MS (ES−): no m/z; retention time: 1.11 min; purity: 88%. $^1$H NMR (DMSO-d6) δ 9.13 (s, 1H), 7.20-7.05 (m, 1H), 6.98 (td, J=7.7, 1.8 Hz, 1H), 6.82-6.70 (m, 2H), 3.76-3.52 (m, 1H), 2.23 (qt, J=7.7, 2.4 Hz, 2H), 2.12-1.97 (m, 2H), 2.00-1.85 (m, 1H), 1.85-1.69 (m, 1H).

Step 3: Synthesis of 4-bromo-2-cyclobutylphenol

To a solution of 2-cyclobutylphenol (29.3 g, 0.15 mol, 1.0 eq.) in DCM (620 mL) was added tetrabutylammonium tribromide (73.3 g, 0.15 mol, 1.0 eq.) and the mixture stirred at room temperature for 1 h. The reaction mixture was quenched with saturated aqueous sodium thiosulphate solution (580 mL) and vigorously stirred at room temperature for 1 h. The organic layer was separated and the aqueous layer re-extracted with further DCM (2×300 mL). The combined organic layers were washed with brine (500 mL), concentrated under reduced pressure and the resulting crude product was washed through a pad of silica gel (7:3 hexanes: DCM (1500 mL) followed by 1:1 hexanes:DCM (1000 mL)) to give the title compound (26.0 g, 0.10 mol, 68%) as a purple oil which was used in the subsequent step without additional purification.

UPLC-MS: acidic 2-minute run MS (ES−): m/z 225.0/ 227.0 (M-H)−; retention time: 1.22 min; purity: 91%. $^1$H NMR (400 MHz, DMSO-d6) δ 9.53 (s, 1H), 7.22 (dd, J=2.5, 0.8 Hz, 1H), 7.14 (dd, J=8.5, 2.5 Hz, 1H), 6.71 (d, J=8.5 Hz, 1H), 3.68-3.55 (m, 1H), 2.23 (qt, J=7.7, 2.3 Hz, 2H), 2.13-1.97 (m, 2H), 2.01-1.86 (m, 1H), 1.77 (m, 1H).

Step 4: Synthesis of methyl 2-(4-bromo-2-cyclobutylphenoxy)-3-methoxypropanoate To a solution of methyl 2-bromo-3-methoxypropanoate (14.7 g, 74.9 mmol, 1.0 eq.) and 4-bromo-2-cyclobutylphenol (17.0 g, 74.9 mmol, 1.0 eq.) in DMF (165 mL) was added potassium carbonate (31.0 g, 224.6 mmol, 3.0 eq.) and the mixture was stirred at room temperature for 4 h. The reaction was diluted with water (200 mL) and extracted with EtOAc (3×200 mL). The combined organic layers were washed sequentially with water (250 mL) and brine (250 mL), dried over sodium sulfate and concentrated under reduced pressure. The crude product was purified by flash chromatography (Si, (Si, 0-7% EtOAc in hexanes) to give the title compound (9.2 g, 26.8 mol, 36%) as a yellow solid.

UPLC-MS: acidic 2-minute run MS (ES−): no m/z; retention time: 1.34 min; purity: 94%. $^1$H NMR (400 MHz, Chloroform-d) δ 7.33 (dd, J=2.5, 0.9 Hz, 1H), 7.22 (ddd, J=8.7, 2.5, 0.6 Hz, 1H), 6.57 (d, J=8.7 Hz, 1H), 4.79 (dd, J=5.6, 3.9 Hz, 1H), 3.97-3.80 (m, 3H), 3.78 (s, 3H), 3.47 (s, 3H), 2.43-2.29 (m, 2H), 2.24-1.96 (m, 3H), 1.92-1.78 (m, 1H).

Step 5: Synthesis of 2-(4-bromo-2-cyclobutylphenoxy)-3-methoxypropanoic acid A solution of methyl 2-(4-bromo-2-cyclobutylphenoxy)-3-methoxypropanoate (9.2 g, 26.8 mmol, 1.0 eq.) in methanol (134 mL) was treated with 1M aqueous sodium hydroxide solution (32.0 mL, 32.0 mmol, 1.2 eq.) and the reaction was stirred at room temperature for 2 h. The mixture was concentrated under reduced pressure to % volume and the resultant aqueous solution washed with DCM (50 mL). The aqueous layer was acidified to pH 4 by the addition of 1M aqueous hydrochloric acid solution then extracted with DCM (3×100 mL). The combined organic layers were dried over sodium sulfate and concentrated under reduced pressure to give the title compound (8.7 g, 26.3 mmol, 99%) as a yellow solid.

UPLC-MS: basic 2-minute run MS (ES−): m/z 327.0/329.0 (M-H)−; retention time: 0.86 min; purity: 100%. $^1$H NMR (DMSO-d$_6$) δ 13.16 (s, 1H), 7.33-7.25 (m, 2H), 6.78-6.71 (m, 1H), 4.93 (dd, J=5.5, 3.0 Hz, 1H), 3.84 (dd, J=11.0, 5.4 Hz, 1H), 3.81-3.60 (m, 2H), 3.35 (s, 3H), 2.33-2.21 (m, 2H), 2.20-1.87 (m, 3H), 1.84-1.71 (m, 1H).

Step 6: Synthesis of sodium (S)-2-(4-bromo-2-cyclobutylphenoxy)-3-methoxypropanoate 2-(4-bromo-2-cyclobutylphenoxy)-3-methoxypropanoic acid (1.5 g, 4.56 mmol) was dissolved to 100 mg/mL in MeCN and purified by chiral Supercritical Fluid Chromatography (SFC) on a Sepiatec Prep SFC 100 model under the following conditions.

Column: Lux A2 (21.2 mm×250 mm, 5 m).

Conditions: 40° C., 50 mL/min, isocratic 75:25 CO$_2$: acetonitrile (0.1% v/v TFA), 100 BarG. Sequential injections of 500 μL (50 mg).

Combined fractions of the enantiomers were evaporated to near dryness using a rotary evaporator, transferred into final vessels with dichloromethane, which was removed on a Biotage V10 at 35° C. before being stored in a vacuum oven at ambient temperature and 5 mbar until constant weight to afford (R)- and (S)-2-(4-bromo-2-cyclopropylphenoxy)-3-methoxypropanoic acid as clear oils.

The resultant separated isomers (ca. 560 mg, 1.7 mmol) were each separately dissolved in MeCN (20 mL) and water (10 mL) then treated with 1M aqueous sodium bicarbonate solution (17.8 mL, 17.8 mmol, 1.05 eq.). After 30 min, the reactions were concentrated under reduced pressure and the resulting solids dried in a vacuum oven at 40° C. overnight to give the title compounds as off-white solids: Sodium (S)-2-(4-bromo-2-cyclobutylphenoxy)-3-methoxypropanoate (572 mg, 1.63 mmol, 36%).

UPLC-MS: acidic 4-minute run MS (ES−): m/z 327.0/329.0 (M-H)−; retention time: 1.92 min; purity: 100%. $^1$H NMR (400 MHz, DMSO-ds) δ 7.22-7.14 (m, 2H), 6.63 (d, J=8.5 Hz, 1H), 4.28 (dd, J=8.0, 2.4 Hz, 1H), 3.76-3.65 (m, 2H), 3.67-3.58 (m, 1H), 3.27 (s, 3H), 2.34-2.18 (m, 3H), 2.08-1.86 (m, 2H), 1.84-1.71 (m, 1H).

Chiral SCF method 2: (S)-enantiomer at 1.427 mins, 99.0% e.e.

Sodium (R)-2-(4-bromo-2-cyclobutylphenoxy)-3-methoxypropanoate (586 mg, 1.67 mmol, 37%).

UPLC-MS and NMR data as for (S)-enantiomer.

Chiral SCF method 2: (R)-enantiomer at 1.817 mins, 99.7% e.e.

Example 6: Electrophysiological Measurement of Compound Inhibition of ClC-1 in Rat Muscle The investigatory goal of these experiments was to evaluate whether compounds inhibit ClC-1 channels in native tissue of rat skeletal muscle fibres. Apparent ClC-1 affinity was reported by the concentration of compound at which 50% of the compound's full inhibition of ClC-1 was observed (EC$_{50}$).

ClC-1 Cl− ion channels generate around 80% of the total membrane conductance ($G_m$) in resting skeletal muscle fibres of most animals including rat and human (Bretag, A H. Muscle chloride channels. Physiological Reviews, 1987, 67, 618-724). Other ion channels that contribute to $G_m$ can therefore be considered negligible, and it is possible to evaluate whether a compound inhibits ClC-1 in rat muscle by comparing $G_m$ measurements before and after exposure to a compound. ClC-1 inhibition would in such recordings be reflected by a reduction of $G_m$.

Experimentally, $G_m$ was measured in individual fibres of whole rat soleus muscles using a three micro-electrodes technique described in this example and in full detail elsewhere (Riisager et al., Determination of cable parameters in skeletal muscle fibres during repetitive firing of action potentials. Journal of Physiology, 2014, 592, 4417-4429). Briefly, intact rat soleus muscles were dissected out from 12-14 week old Wistar rats and placed in an experimental chamber that was perfused with a standard Krebs Ringer solution containing 122 mM NaCl, 25 mM NaHCO$_3$, 2.8 mM KCl, 1.2 mM KH$_2$PO$_4$, 1.2 mM MgSO$_4$, 1.3 mM CaCl$_2$, 5.0 mM D-glucose. During experiments, the solution was kept at approx. 30° C. and continuously equilibrated with a mixture of 95% O$_2$ and 5% CO$_2$, pH ~7.4. The experimental chamber was placed in Nikon upright microscope that was used to visualize individual muscle fibres and the three electrodes (glass pipettes filled with 2 M potassium citrate). For $G_m$ measurements, the electrodes were inserted into the same fibre with known inter-electrode distances of 0.35-0.5 mm (V1-V2, X1) and 1.1-1.5 mm (V1-V3, X3) (FIG. 1A). The membrane potential of the impaled muscle fibre was recorded by all electrodes. Two of the electrodes were furthermore used to inject 50 ms current pulses of −30 nA. Given the positions of the electrodes, three different inter-electrode distances could be identified (X1-X2, X1-X3, X2-X3) and hence the membrane potential responses to the current injections could be obtained at three distances from the point of current injection. The steady state voltage deflection at each distance was divided by the magnitude of current injected (−30 nA) and the resulting transfer resistances were plotted against inter-electrode distance and the data was fitted to a mono-exponential function from which $G_m$ could be calculated using linear cable theory (FIG. 1B).

To establish a dose response relationship, $G_m$ was first determined in 10 muscle fibres in the absence of compound and then at four increasing compound concentrations with $G_m$ determinations in 5-10 fibres at each concentration. The average $G_m$ values at each concentration were plotted against compound concentration and the data was fitted to sigmoidal function to obtain an EC$_{50}$ value (FIG. 1C). Table 2 shows the EC$_{50}$ values for a range of compounds with n values referring to number of experiments that each reflect recordings from around 50 fibres.

TABLE 2

Inhibition of ClC-1 ion channel using compounds of the disclosure

| Compound investigated | EC$_{50}$ (μM) |
|---|---|
| Compound A-1 | 3.7 ± 0.2 (n = 3) |
| Compound A-6 | 3.2 ± 2.1 (n = 5) |

Example 7: Measurement of Force in an In Vitro Model

The current disclosure relates to compounds that inhibit ClC-1 ion channels and increase muscle excitability and thereby improve muscle function in clinical conditions where muscle activation is failing. Such conditions result in loss of contractile function of skeletal muscle, weakness and excessive fatigue. In this series of experiments the compounds were tested for their ability to restore contractile function of isolated rat muscle when the neuromuscular transmission had been compromised akin to neuromuscular disorders.

Experimentally, soleus muscles from 4-5 week old rats were isolated with the motor nerve remaining attached. The nerve-muscle preparations were mounted in experimental setups that enabled electrical stimulation of the motor nerve. Stimulation of the motor nerve led to activation of the muscle fibres and ensuing force production that was recorded. The nerve-muscle preparations were also in these experiments incubated in the standard Krebs Ringer (see example 5) and the solution was heated to 30° C. and continuously equilibrated with a mixture of 95% $O_2$ and 5% $CO_2$, pH ~7.4.

Figure 2:
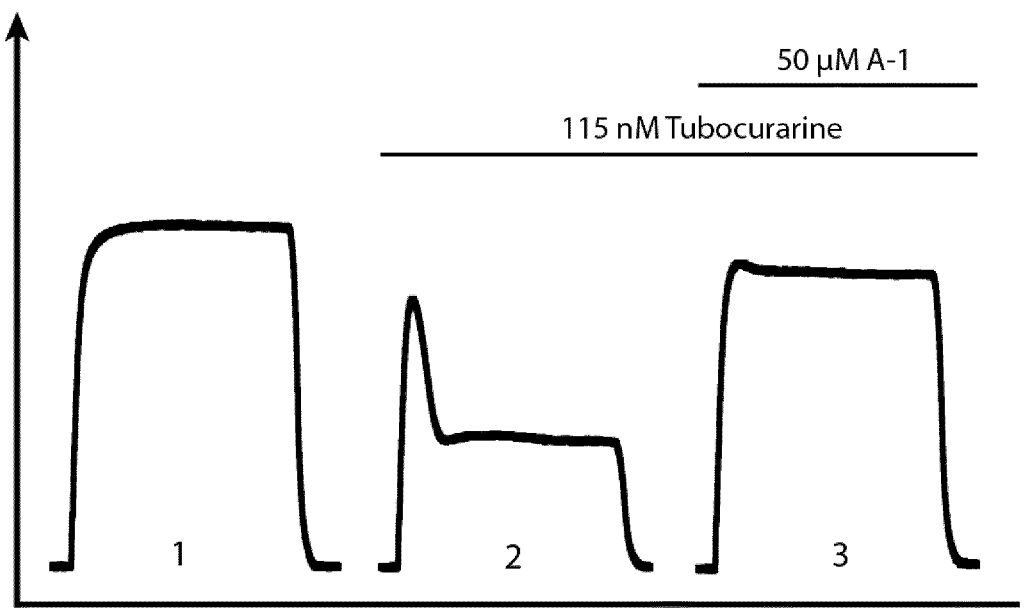
FIG. 2. Panel A shows representative force traces before and after exposure to compound A-1. Force traces from a representative muscle stimulated to contract in 1) control condition before addition of neuromuscular blocking agent, 2) the force response to stimulation after 90 minutes incubation with Tubocurarine. Here the muscle displays severe neuromuscular transmission impediment, and 3) The muscle force response after addition of 50 µM compound A-1. Panel B shows average force (AUC) from 3 muscles relative to their initial force. The traces presented in panel A (1, 2, 3), correspond to the dotted lines in panel B, respectively. Thus, force is lost due to 90 min incubation in tubocurarine and is subsequently recovered when compound A-1 is added.
Figure 2:
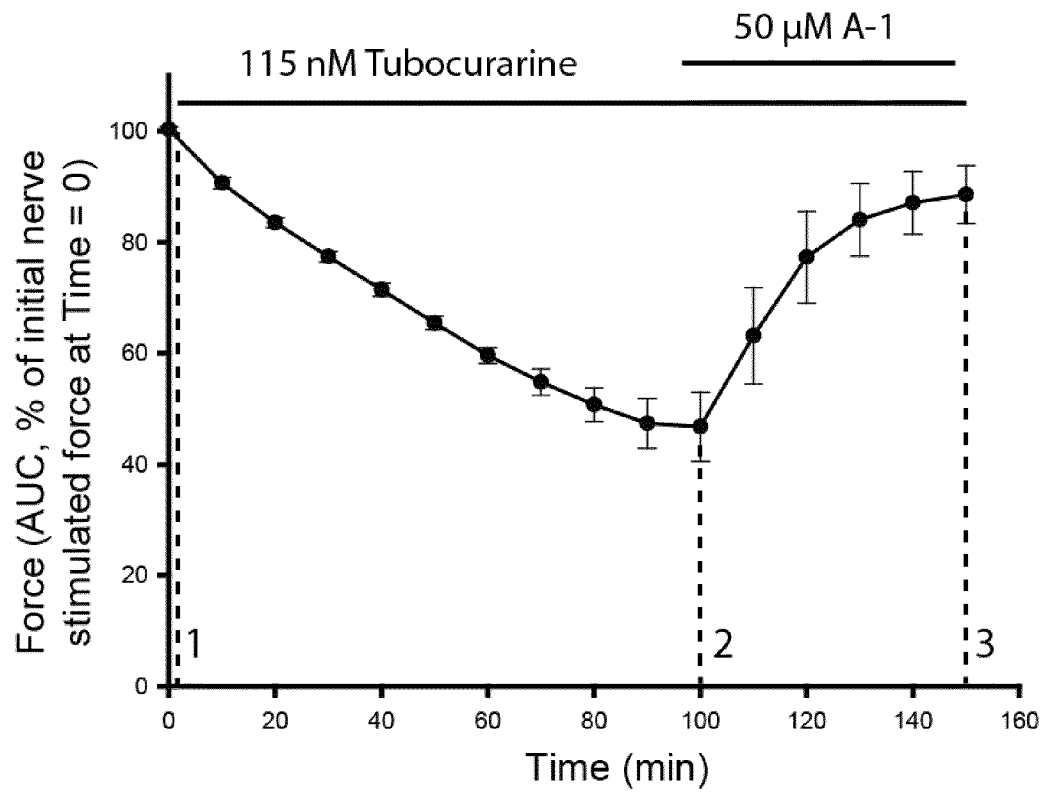

After mounting the nerve-muscle preparation in the experimental setup, the contractile function of the muscle was initially assessed under the control conditions (FIG. 2A). Sub-maximal concentration of tubocurarine (115 nM), an acetylcholine receptors antagonist, was then added to the experimental bath to impose partial inhibition of the ability of the motor nerve to activate the muscle fibres. The experimental condition mimics the failing neuromuscular transmission in a range of neuromuscular disorders. After addition of tubocurarine the contractile force declined over the next 90 mins to 10-50% of the control force. 50 µM of the test compound was then added and the contractile force recovered despite the continued presence of tubocurarine. To quantify the ability of the compound to restore force the percentage of the initial force that was restored was determined after 40 mins of compound exposure (FIG. 2B) and the point increase is reported in Table 3.

TABLE 3

Percentage increase of initial force that was restored

| Compound investigated | Point increase (%) |
|---|---|
| A-1 | 36.3* |
| (2R)-A-1 | 0.2 |
| A-2 | 22.3 ± 3.8 (n = 2) |
| (2R)-A-2 | −2.1 (n = 1) |
| A-6 | 35.6 ± 8.3 (n = 7) |
| (2R)-A-6 | −4.1 ± 1.4 (n = 3) |

*the compound was tested 1 more time giving an average force increase of 40.1 ± 5.3 (n = 2)

In conclusion, this example demonstrates that the compounds of the present disclosure are able to increase muscle excitability and thereby improve muscle function in clinical conditions. In comparison, the (2R)-enantiomer was unable to recover force compared to the (2S)-enantiomers.

Example 8: Measurement of In Situ Muscle Contractile Characteristics

Isometric hindlimb force was measured in 12-week old female Lewis rats in the presence and absence of compound.

Rats were placed under anesthesia with isoflurane (2-4%), intubated and subsequently connected to a micro ventilator (Microvent 1, Hallowell EMC, US). Two stimulation electrodes were inserted through the skin to stimulate the sciatic nerve. A small incision was made proximal to the ankle, to expose the Achilles tendon, which was tied by cotton string, and connected to a force transducer (Fort250, World Precision Instruments) with adjustable position (Vernier control). The Achilles tendon was then cut distal to the attached cotton string. The rat was placed on a heated pad, and to prevent movement artefacts from contraction of the ankle dorsiflexors, the foot was fixated by tape on a footplate.

Muscle contractile properties were assessed by applying an electrical current (under supramaximal voltage conditions) to the nerve and recording the force generated by the muscle. The muscle was stretched until maximal force was obtained, when assessed by 2 Hz stimulation. Isometric force was measured every 30 seconds at 12 Hz (Twitch), 10 pulses, and at every 5 minutes at 80 Hz (Tetanic) for 1 second (80 pulses). This stimulation pattern was employed throughout the experiment, expect in few cases where 80 Hz stimulation was replaced by 12 Hz (10 pulses). Neuromuscular transmission was partially inhibited by constant infusion of Cisatracurium (Nimbex, GlaxoSmithKline) at a concentration of 0.1 mg/kg at an adjustable infusion speed, adjusted individually for each animal to obtain a level of inhibition of ca. 50% of the forced generated at 12 Hz stimulation on the $4^{th}$ pulse. When the level of neuromuscular inhibition was stable, the test article was injected i.v. at the chosen concentration. The effect of test article was assessed on its ability to increase force generated from the stimulation pattern applied. The effect was assessed in the ability to increase force per se (tetanic, 80 Hz, stimulation), and the ratio between individual twitch peaks (12 Hz stimulation). The effect was monitored for at least 1 hour after injection of test article. In addition, the time from injection of test article to maximal effect on force (both twitch and tetanic) was noted and the time for the effect to disappear (return to baseline), if possible. When appropriate the infusion of neuromuscular blocking agent was ceased, with the stimulation pattern continued, and the return of force to control levels was monitored. Animals were sacrificed by cervical dislocation while still fully sedated.

Compound A-1 was dosed 47.2 mg/kg i.v. resulting in an increase in tetanic force of 85%. This demonstrates that compounds of the disclosure, such as Compounds A-1, can restore force to muscles in vivo which have been partially inhibited by a neuromuscular blocker.

The invention claimed is:
1. A compound of Formula (I):

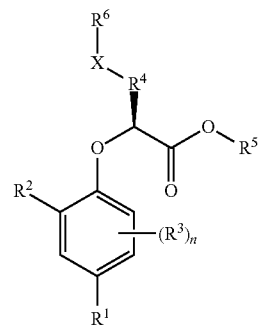

Formula (I)

wherein:
R$^1$ is selected from the group consisting of F, Cl, Br and I;
R$^2$ is selected from the group consisting of $C_{2-5}$ alkyl optionally substituted with one or more, identical or different, substituents R$^8$ and $C_{3-5}$ cycloalkyl optionally substituted with one or more, identical or different, substituents R⁸ and wherein one —CH₂— in the C$_{2-5}$ alkyl or C$_{3-5}$ cycloalkyl is optionally replaced by —O—;

R³ is selected from the group consisting of deuterium, Cl and F;

R⁴ is C$_{1-3}$ alkanediyl, which may be optionally substituted with one or more, identical or different, substituents R⁸, R⁵ is selected from the group consisting of H, C$_{1-5}$ alkyl, C$_{2-5}$ alkenyl, C$_{2-5}$ alkynyl, and C$_{3-6}$ cycloalkyl, each of which may be optionally substituted with one or more, identical or different, substituents R⁷; phenyl optionally substituted with one or more, identical or different, substituents R⁹; and benzyl optionally substituted with one or more, identical or different, substituents R⁹;

R⁶ is selected from the group consisting of C$_{1-5}$ alkyl and C$_{3-5}$ cycloalkyl, each of which may be optionally substituted with one or more, identical or different, substituents R⁷;

R⁷ is independently selected from the group consisting of deuterium and F; —R⁸ is independently selected from the group consisting of deuterium, F and C$_{1-3}$ alkyl optionally substituted with one or more, identical or different, substituents R⁷;

R⁹ is independently selected from the group consisting of deuterium, methoxy, nitro, cyano, Cl, Br, I and F; and n is an integer 0, 1, 2 or 3; and X is O, S, SO or SO₂;

or a pharmaceutically acceptable salt, hydrate, polymorph, tautomer, or solvate thereof; with the proviso that when R¹ is Br, R² is isopropyl, R⁴ is methylene, R⁵ is H, R⁶ is CH₃, and X is O then n is not zero.

2. The compound according to claim 1, wherein R¹ is Cl or Br.

3. The compound according to claim 1, wherein R² is C$_{2-5}$ alkyl optionally substituted with one or more, identical or different, substituents R⁷.

4. The compound according to claim 1, wherein R² is C$_{3-5}$ cycloalkyl optionally substituted with one or more, identical or different, substituents R⁸.

5. The compound according to claim 1, wherein R⁴ is methylene.

6. The compound according to claim 1, wherein R⁵ is H.

7. The compound according to claim 1, wherein R⁶ is C$_{1-5}$ alkyl optionally substituted with one or more, identical or different, substituents R⁷.

8. The compound according to claim 1, wherein R⁶ is C$_{3-5}$ cycloalkyl optionally substituted with one or more, identical or different, substituents R⁷.

9. The compound according to claim 1, wherein n is 0.

10. The compound according to claim 1, wherein X is O or S.

11. The compound according to claim 1, wherein the compound is selected from the group consisting of:

(2S)-2-(4-bromo-2-cyclopropylphenoxy)-3-methoxypropanoic acid;

(2S)-2-(4-bromo-2-cyclopropylphenoxy)-3-ethoxypropanoic acid;

(2S)-2-(4-bromo-2-cyclopropyl-5-fluorophenoxy)-3-methoxypropanoic acid; (2S)-2-[4-bromo-2-(1-ethylcyclopropyl) phenoxy]-3-methoxypropanoic acid; (2S)-2-(4-bromo-2-cyclopropylphenoxy)-3-(difluoromethoxy) propanoic acid;

(2S)-2-(4-chloro-2-cyclopropylphenoxy)-3-methoxypropanoic acid;

(2S)-2-(4-bromo-2-cyclopropylphenoxy)-3-methoxybutanoic acid;

(2S, 3S)-2-(4-chloro-2-cyclopropyl-5-fluorophenoxy)-3-methoxypropanoic acid; (2R)-2-(4-bromo-2-cyclobutylphenoxy)-3-(methylsulfanyl) propanoic acid;

(2S)-2-(4-bromo-2-cyclobutylphenoxy)-3-methoxypropanoic acid;

(2S)-2-(4-bromo-2-cyclopropylphenoxy)-4-methoxybutanoic acid; and (2R)-2-(4-bromo-2-cyclopropylphenoxy)-3-(methylsulfanyl) propanoic acid; and (2S)-2-[4-bromo-2-(propan-2-yl) phenoxy]-3-methoxypropanoic acid.

12. The compound according to claim 1, wherein the compound is an inhibitor of the ClC-1 ion channel.

13. A composition comprising the compound of Formula (D):

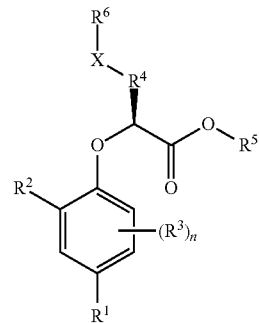

Formula (I)

wherein:

R¹ is selected from the group consisting of F, Cl, Br and I;

R² is selected from the group consisting of C$_{2-5}$ alkyl optionally substituted with one or more, identical or different, substituents R⁸ and C$_{3-5}$ cycloalkyl optionally substituted with one or more, identical or different, substituents R⁸ and wherein one —CH₂— in the C$_{2-5}$ alkyl or C$_{3-5}$ cycloalkyl is optionally replaced by —O—;

R³ is selected from the group consisting of deuterium, Cl and F;

R⁴ is C$_{1-3}$ alkanediyl, which may be optionally substituted with one or more, identical or different, substituents R⁸;

R⁵ is selected from the group consisting of H, C$_{1-5}$ alkyl, C$_{2-5}$ alkenyl, C$_{2-5}$ alkynyl, and C$_{3-6}$ cycloalkyl, each of which may be optionally substituted with one or more, identical or different, substituents R⁷; phenyl optionally substituted with one or more, identical or different, substituents R⁹; and benzyl optionally substituted with one or more, identical or different, substituents R⁹;

R⁶ is selected from the group consisting of C$_{1-5}$ alkyl and C$_{3-5}$ cycloalkyl, each of which may be optionally substituted with one or more, identical or different, substituents R⁷;

R⁷ is independently selected from the group consisting of deuterium and F; —R⁸ is independently selected from the group consisting of deuterium, F and C$_{1-3}$ alkyl optionally substituted with one or more, identical or different, substituents R⁷;

$R^9$ is independently selected from the group consisting of deuterium, methoxy, nitro, cyano, Cl, Br, I and F; and n is an integer 0, 1, 2 or 3; and X is O, S, SO or $SO_2$;

or a pharmaceutically acceptable salt, hydrate, polymorph, tautomer, or solvate thereof;

with the proviso that when $R^1$ is Br, $R^2$ is isopropyl, $R^4$ is methylene, $R^5$ is H, $R^6$ is $CH_3$, and X is O then n is not zero;

and a pharmaceutically acceptable carrier.

14. The compound according to claim 1 for use as a medicament.

15. A method of treating a patient comprising administering to the patient a therapeutically effective amount of a compound of Formula (I):

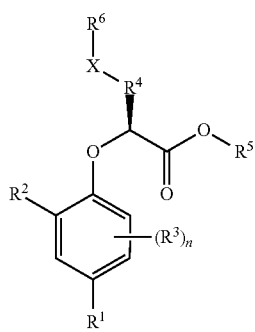

Formula (I)

wherein:
R$^1$ is selected from the group consisting of F, Cl, Br and I;

R$^2$ is selected from the group consisting of C$_{2-5}$ alkyl optionally substituted with one or more, identical or different, substituents R$^8$ and C$_{3-6}$ cycloalkyl optionally substituted with one or more, identical or different, substituents R$^8$ and wherein one —CH$_2$— in the C$_{2-5}$ alkyl or C$_{3-5}$ cycloalkyl is optionally replaced by —O—;

R$^3$ is selected from the group consisting of deuterium, Cl and F;

R$^4$ is C$_{1-3}$ alkanediyl, which may be optionally substituted with one or more, identical or different, substituents R$^8$;

R$^5$ is selected from the group consisting of H, C$_{1-5}$ alkyl, C$_{2-5}$ alkenyl, C$_{2-5}$ alkynyl, and C$_{3-6}$ cycloalkyl, each of which may be optionally substituted with one or more, identical or different, substituents R$^7$; phenyl optionally substituted with one or more, identical or different, substituents R$^9$; and benzyl optionally substituted with one or more, identical or different, substituents R$^9$;

R$^6$ is selected from the group consisting of C$_{1-5}$ alkyl and C$_{3-5}$ cycloalkyl, each of which may be optionally substituted with one or more, identical or different, substituents R$^7$;

R$^7$ is independently selected from the group consisting of deuterium and F; —R$^8$ is independently selected from the group consisting of deuterium, F and C$_{1-3}$ alkyl optionally substituted with one or more, identical or different, substituents R$^7$;

R$^9$ is independently selected from the group consisting of deuterium, methoxy, nitro, cyano, Cl, Br, I and F; and n is an integer 0, 1, 2 or 3; and X is O, S, SO or $SO_2$;

or a pharmaceutically acceptable salt, hydrate, polymorph, tautomer, or solvate thereof;

with the proviso that when $R^1$ is Br, $R^2$ is isopropyl, $R^4$ is methylene, $R^5$ is H, $R^6$ is $CH_3$, and X is O then n is not zero, for use in the treatment of symptoms of an indication selected from the group consisting of myasthenia gravis, Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barre syndrome, poliomyelitis, post-polio syndrome, chronic fatigue syndrome, critical illness polyneuropathy, periodic paralysis, sarcopenia, hypokalemic periodic paralysis and hyperkalemic periodic paralysis.

16. A method of reversing and/or ameliorating a neuromuscular blockade in a patient comprising administering to the patient a therapeutically effective amount of a compound of Formula (I):

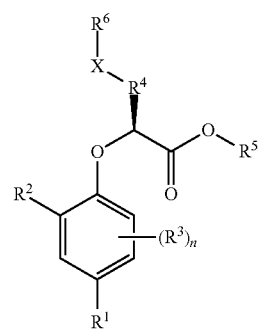

Formula (I)

wherein:
R$^1$ is selected from the group consisting of F, Cl, Br and I;

R$^2$ is selected from the group consisting of C$_{2-5}$ alkyl optionally substituted with one or more, identical or different, substituents R$^8$ and C$_{3-5}$ cycloalkyl optionally substituted with one or more, identical or different, substituents R$^8$ and wherein one —CH$_2$— in the C$_{2-5}$ alkyl or C$_{3-5}$ cycloalkyl is optionally replaced by —O—;

R$^3$ is selected from the group consisting of deuterium, Cl and F;

R$^4$ is C$_{1-3}$ alkanediyl, which may be optionally substituted with one or more identical or different, substituents R$^8$;

R$^5$ is selected from the group consisting of H, C$_{1-5}$ alkyl, C$_{2-5}$ alkenyl, C$_{2-5}$ alkynyl, and C$_{3-6}$ cycloalkyl, each of which may be optionally substituted with one or more, identical or different, substituents R$^7$; phenyl optionally substituted with one or more, identical or different, substituents R$^9$; and benzyl optionally substituted with one or more, identical or different, substituents R$^9$;

R$^6$ is selected from the group consisting of C$_{1-5}$ alkyl and C$_{3-5}$ cycloalkyl, each of which may be optionally substituted with one or more, identical or different, substituents R$^7$;

R$^7$ is independently selected from the group consisting of deuterium and F; —R$^8$ is independently selected from the group consisting of deuterium, F and C$_{1-3}$ alkyl optionally substituted with one or more, identical or different, substituents $R^7$;

$R^9$ is independently selected from the group consisting of deuterium, methoxy, nitro, cyano, Cl, Br, I and F; and n is an integer 0, 1 2 or 3; and X is O, S, SO or $SO_2$;

or a pharmaceutically acceptable salt, hydrate, polymorph, tautomer, or solvate thereof, with the proviso that when R' is Br, $R^2$ is isopropyl, $R^4$ is methylene, $R^5$ is H, $R^6$ is $CH_3$, and X is O then n is not zero, for use in reversing and/or ameliorating a neuromuscular blockade.

17. The compound of claim 1 wherein $R^1$ is Cl or Br, $R^2$ is $C_{2-5}$ alkyl optionally substituted with one or more, identical or different, substituents $R^7$ or substituents $R^8$, $R^4$ is methylene, and $R^5$ is H.

18. The compound of claim 17 wherein Re is $C_{1-5}$ alkyl optionally substituted with one or more, identical or different, substituents $R^7$.

19. The compound according to claim 18 wherein n is 0.

20. The compound according to claim 19 wherein X is O or S.

* * * * *